(12) United States Patent
Barrow et al.

(10) Patent No.: US 7,745,452 B2
(45) Date of Patent: Jun. 29, 2010

(54) QUINAZOLINONE T-TYPE CALCIUM CHANNEL ANTAGONISTS

(75) Inventors: James C. Barrow, Harleysville, PA (US); Rowena V. Cube, Harleysville, PA (US); Phung Le Ngo, Lansdale, PA (US); Kenneth E. Rittle, Green Lane, PA (US); Zhiqiang Yang, Schwenksville, PA (US); Steven D. Young, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 33 days.

(21) Appl. No.: 11/886,053

(22) PCT Filed: Mar. 8, 2006

(86) PCT No.: PCT/US2006/008177

§ 371 (c)(1),
(2), (4) Date: Sep. 7, 2007

(87) PCT Pub. No.: WO2006/098969

PCT Pub. Date: Sep. 21, 2006

(65) Prior Publication Data

US 2008/0167329 A1    Jul. 10, 2008

(51) Int. Cl.
*C07D 473/00* (2006.01)
(52) U.S. Cl. .................. 514/266.3; 544/286
(58) Field of Classification Search ............ 514/266.3; 544/286
See application file for complete search history.

(56) References Cited

U.S. PATENT DOCUMENTS

2006/0003985 A1    1/2006  Renger et al.

2007/0010537 A1    1/2007  Hamamura et al.

FOREIGN PATENT DOCUMENTS

| DE | 4320347 | 12/1994 |
| EP | 0530994 | 3/1993 |
| WO | WO93/04047 | 3/1993 |
| WO | WO 2004/035000 | * 4/2004 |

OTHER PUBLICATIONS

Patani, et al. Chem. Rev., 96, 1996, pp. 3147-3176.*
S. J. Park et al., "Synthesis and SAR Studies of a Novel Series of T-type Calcium Channel Blockers", J. Bioorg. Med. Chem, 2006, pp. 1-10.

* cited by examiner

*Primary Examiner*—James O Wilson
*Assistant Examiner*—Douglas M Willis
(74) *Attorney, Agent, or Firm*—J. Eric Thies; Gerard M. Devlin

(57) ABSTRACT

The present invention is directed to quinazolinone compounds of the formula I:

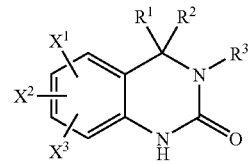

wherein $R^1$, $R^2$, $R^3$, $X^1$, $X^2$, $X^3$ are defined herein. These compounds are antagonists of T-type calcium channels, and are useful in the treatment or prevention of disorders and diseases in which T-type calcium channels are involved. The invention is also directed to pharmaceutical compositions comprising these compounds and the use of these compounds and compositions in the prevention or treatment of such diseases in which T-type calcium channels are involved.

12 Claims, No Drawings

QUINAZOLINONE T-TYPE CALCIUM CHANNEL ANTAGONISTS

CROSS REFERENCE TO RELATED APPLICATIONS

This application is a U.S. National Phase application under 35 U.S.C. §371 of PCT Application No. PCT/US2006/008177, filed Mar. 8, 2006, which claims priority under 35 U.S.C. §119 from U.S. Application No. 60/659,954, filed Mar. 9, 2005.

BACKGROUND OF THE INVENTION

Plasma membrane calcium channels are members of a diverse superfamily of voltage gated channel proteins. Calcium channels are membrane-spanning, multi-subunit proteins that allow controlled entry of Ca2+ ions into cells from the extracellular fluid. Excitable cells throughout the animal kingdom, and at least some bacterial, fungal and plant cells, possess one or more types of calcium channel. Nearly all "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels Multiple types of calcium channels have been identified in mammalian cells from various tissues, including skeletal muscle, cardiac muscle, lung, smooth muscle and brain. A major type of this family are the L-type calcium channels, whose function is inhibited by the familiar classes of calcium channel blockers (dihydropyridines such as nifedipine, phenylalkylamines such as verapamil, and benzothiazepines such as diltiazem). Additional classes of plasma membrane calcium channels are referred to as T, N, P, Q and R.

The "T-type" (or "low voltage-activated") calcium channels are so named because their openings are of briefer duration (T=transient) than the longer (L=long-lasting) openings of the L-type calcium channels. The L, N, P and Q-type channels activate at more positive potentials (high voltage activated) and display diverse kinetics and voltage-dependent properties. There are three subtypes of T-type calcium channels that have been molecularly, pharmacologically, and electrophysiologically identified from various warm blooded animals including rat [J Biol. Chem. 276(6) 3999-4011 (2001); Eur J Neurosci 11(12):4171-8 (1999); reviewed in Cell Mol Life Sci 56(7-8):660-9 (1999)]. These subtypes have been termed α1G, α1H, and α1I. The molecular properties of these channels demonstrate that the amino acid sequences are between 60-70% identical. The electrophysiological characterization of these individual subtypes has revealed differences in their voltage-dependent activation, inactivation, deactivation and steady-state inactivation levels and their selectivities to various ions such as barium (J Biol. Chem. 276(6) 3999-4011 (2001)). Pharmacologically, these subtypes also have differing sensitivities to blockade by ionic nickel. These channel subtypes are also expressed in various forms due to their ability to undergo various splicing events during their assembly (J Biol. Chem. 276(6) 3999-4011 (2001)).

T-type calcium channels have been implicated in pathologies related to various diseases and disorders, including epilepsy, essential tremor, pain, neuropathic pain, schizophrenia, Parkinson's disease, depression, anxiety, sleep disorders, sleep disturbances, psychosis, schizophreniac, cardiac arrhythmia, hypertension, certain types of cancer, diabetes, infertility and sexual dysfunction (J Neuroscience, 14, 5485 (1994); Drugs Future 30(6), 573-580 (2005); EMBO J, 24, 315-324 (2005)). The known therapeutic regimens for such treating such diseases and disorders suffer from numerous problems. Accordingly, a more physiological way to treat these diseases and disorders would be highly desirable.

SUMMARY OF THE INVENTION

The present invention is directed to quinazolinone compounds which are antagonists of T-type calcium channels, and which are useful in the treatment or prevention of neurological and psychiatric disorders and diseases in which T-type calcium channels are involved. The invention is also directed to pharmaceutical compositions comprising these compounds and the use of these compounds and compositions in the prevention or treatment of such diseases in which T-type calcium channels are involved.

DETAILED DESCRIPTION OF THE INVENTION

The present invention is directed to compounds of the formula I:

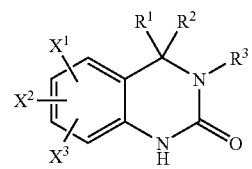

wherein:
$X^1$, $X^2$ and $X^3$ are independently selected from the group consisting of:
  (1) hydrogen,
  (2) fluoro,
  (3) chloro, and
  (4) bromo;
$R^1$ is phenyl, $C_{1-6}$alkyl, or $C_{3-6}$cycloalkyl, which is unsubstituted or substituted with a substituent selected from the group consisting of:
  (1) halogen,
  (2) $C_{1-6}$alkyl, which is unsubstituted or substituted with halogen, hydroxyl or phenyl,
  (3) —$OC_{1-6}$alkyl, which is unsubstituted or substituted with halogen, hydroxyl or phenyl,
  (4) —CN,
  (5) —$NR^5R^6$, wherein $R^5$ and $R^6$ are independently selected from hydrogen, $C_{1-6}$alkyl and $C_{1-6}$alkyl-phenyl, and
  (6) —$S(O)_nC_{1-6}$alkyl, wherein n is 0, 1 or 2;
$R^2$ is $C_{1-6}$alkyl, $C_{3-6}$cycloalkyl, phenyl, $C_{2-6}$alkenyl, or $C_{2-6}$alkynyl, which is unsubstituted or substituted with one or more substituents selected from the group consisting of:
  (1) fluoro,
  (2) chloro,
  (3) —$OC_{1-6}$alkyl, which is unsubstituted or substituted with halogen, hydroxyl or phenyl,
  (4) —$S(O)_nC_{1-6}$alkyl,
  (5) —OH,
  (6) =O,
  (7) —CHO,
  (8) —$CO_2$—$C_{1-6}$alkyl,
  (9) $C_{3-6}$cycloalkyl,
  (10) dioxanyl, and

(11) phenyl, which is unsubstituted or substituted with halogen, hydroxyl, $C_{1-6}$alkyl or —O—$C_{1-6}$alkyl;

$R^3$ is $C_{1-6}$alkyl which is substituted with one or more fluoro, and which is optionally substituted with an additional substituent selected from the group consisting of:
(1) $C_{1-6}$alkyl,
(2) $C_{3-6}$cycloalkyl,
(3) phenyl, and
(4) pyridyl;

and pharmaceutically acceptable salts thereof and individual diastereomers thereof.

An embodiment of the present invention includes compounds wherein
$X^1$ is selected from the group consisting of:
(1) fluoro,
(2) chloro, and
(3) bromo;
$X^2$ is selected from the group consisting of:
(1) fluoro,
(2) chloro, and
$X^3$ is hydrogen.

An embodiment of the present invention includes compounds wherein $X^1$ is fluoro, $X^2$ is hydrogen and $X^3$ is hydrogen.

An embodiment of the present invention includes compounds wherein $X^1$ is fluoro, $X^2$ is fluoro and $X^3$ is hydrogen.

An embodiment of the present invention includes compounds wherein $X^1$ is 6-fluoro, $X^2$ is hydrogen and $X^3$ is hydrogen.

An embodiment of the present invention includes compounds wherein $X^1$ is 6-fluoro, $X^2$ is 5-fluoro and $X^3$ is hydrogen An embodiment of the present invention includes compounds wherein $X^1$ is chloro, $X^2$ is hydrogen and $X^3$ is hydrogen.

An embodiment of the present invention includes compounds wherein $X^1$ is chloro, $X^2$ is fluoro and $X^3$ is hydrogen.

An embodiment of the present invention includes compounds wherein $X^1$ is 6-chloro, $X^2$ is hydrogen and $X^3$ is hydrogen.

An embodiment of the present invention includes compounds wherein $X^1$ is 6-chloro, $X^2$ is 5-fluoro and $X^3$ is hydrogen An embodiment of the present invention includes compounds wherein $R^1$ is phenyl or cyclopropyl, which is unsubstituted or substituted with a substituent selected from the group consisting of:
(1) fluoro,
(2) chloro,
(3) $CH_3$,
(4) $CF_3$,
(5) $OCF_3$,
(6) $OCH_3$, and
(7) —$N(CH_3)_2$.

An embodiment of the present invention includes compounds wherein $R^1$ is phenyl, which is unsubstituted or substituted with fluoro, methyl or methoxy.

An embodiment of the present invention includes compounds wherein $R^1$ is phenyl.

An embodiment of the present invention includes compounds wherein $R^1$ is para-fluorophenyl.

An embodiment of the present invention includes compounds wherein $R^1$ is cyclopropyl.

An embodiment of the present invention includes compounds wherein $R^2$ is selected from the group consisting of:

(1) $CH_2CH_3$,
(2) $CH_2CH_2CH_3$,
(3) cyclopropyl,
(4) $CF_3$,
(5) $CH_2CF_3$,
(6) $CH_2CHF_2$,
(7) $CH_2C(CH_3)_3$,
(8) $CH_2CH=CH_2$,
(9) $C=CH_2(CH_3)$,
(10) $CH_2C=CCH_3$,
(11) —$CO_2$—$CH_3$,
(12) $CH_2OCH_2CH_3$,
(13) $CH_2CH_2CH_2CH_3$,
(14) $CH_2CH_2$-dioxanyl, and
(15) $CH_2C(CH_3)_2$-phenyl.

An embodiment of the present invention includes compounds wherein $R^2$ is $CH_2CH_3$, An embodiment of the present invention includes compounds wherein $R^2$ is $CH_2CH_2CH_3$. An embodiment of the present invention includes compounds wherein $R^2$ is $CF_3$.

An embodiment of the present invention includes compounds wherein $R^3$ is selected from the group consisting of:
(1) $CF_3$,
(2) $CF_2H$,
(3) $CH_2CF_3$,
(4) $CH_2CHF_2$,
(5) $CH_2CH_2F$,
(6) $CH_2CF_2CH_3$,
(6) $CH_2CF_2CF_3$,
(7) $CH_2CF_2$-phenyl, and
(8) $CH_2CF_2$-pyridyl.

An embodiment of the present invention includes compounds wherein $R^3$ is $CH_2CF_3$. An embodiment of the present invention includes compounds wherein $R^3$ is $CH_2CHF_2$.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halo or halogen as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonizing T-type calcium channel activity in a patient such as a mammal in need of such inhibition comprising the administration of an effective amount of the compound. The present invention is directed to the use of the compounds disclosed herein as antagonists of T-type calcium channels activity. In addition to primates, especially humans, a variety of other mammals can be treated according to the method of the present invention.

The present invention is further directed to a method for the manufacture of a medicament for antagonizing T-type calcium channels activity or treating the disorders and diseases noted herein in humans and animals comprising combining a compound of the present invention with a pharmaceutical carrier or diluent.

The subject treated in the present methods is generally a mammal, preferably a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as T-type calcium channel antagonists may be readily determined without undue experimentation by methodology well known in the art, including the "FLIPR $Ca^{2+}$ Flux Assay" and the "T-type Calcium ($Ca^{2+}$) Antagonist Voltage-Clamp Assay" [described by Xia, et al., Assay and Drug Development Tech., 1(5), 637-645 (2003)]. In a typical experiment ion channel function from HEK 293 cells expressing the T-type channel alpha-1G, H, or I (CaV 3.1, 3.2, 3.3) is recorded to determine the activity of compounds in blocking the calcium current mediated by the T-type channel alpha-1G, H, or I (CaV 3.1, 3.2, 3.3). In this T-type calcium ($Ca^{2+}$) antagonist voltage-clamp assay calcium currents are elicited from the resting state of the human alpha-1G, H, or I (CaV 3.1, 3.2, 3.3) calcium channel as follows. Sequence information for T-type (Low-voltage activated) calcium channels are fully disclosed in e.g., U.S. Pat. Nos. 5,618,720, 5,686,241, 5,710,250, 5,726,035, 5,792,846, 5,846,757, 5,851,824, 5,874,236, 5,876,958, 6,013,474, 6,057,114, 6,096,514, WO 99/28342, and J. Neuroscience, 19(6):1912-1921 (1999). Cells expressing the T-type channels were grown in growth media which comprised: DMEM, 10% Tet-system approved FBS (Clontech Laboratories Inc.), 100 microgram/ml Penicillin/Streptomycin, 2 mM L-Glutamine, 150 microgram/ml Zeocin, 5 microgram/ml Blasticidin. T-channel expression was induced by exposing the cells to 2 mM Tetracycline for 24 hrs. Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier. Trypsinization buffer was 0.05% Trypsin, 0.53 mM EDTA. The extracellular recording solution consists of (mM): 130 mM NaCl, 4 mM KCl, 1 mM $MgCl_2$, 2 mM $CaCl_2$, 20 mM HEPES, 30 Glucose, pH 7.4. The internal solution consists of (mM): 125 CsCl, 10 TEA-Cl, 10 HEPES, 8 NaCl, 0.06 $CaCl_2$, 0.6 EGTA, 4 ATP-Mg, 0.3 GTP; 135 mM CsMeSO3, 1 MgCl2, 10 CsCl, 5 EGTA, 10 HEPES, pH 7.4; or 135 mM CsCl, 2 MgCl2, 3 MgATP, 2 Na2ATP, 1 Na2GTP, 5 EGTA, 10 HEPES, pH 7.4. Upon insertion of the pipette tip into the bath, the series resistance is noted (acceptable range is between 1-4 megaohm). The junction potential between the pipette and bath solutions is zeroed on the amplifier. The cell is then patched, the patch broken, and, after compensation for series resistance (>=80%), the voltage protocol is applied while recording the whole cell $Ca^{2+}$ current response. Voltage protocols: (1) −80 mV holding potential every 20 seconds pulse to −20 mV for 70 msec duration; the effectiveness of the drug in inhibiting the current mediated by the channel is measured directly from measuring the reduction in peak current amplitude initiated by the voltage shift from −80 mV to −20 mV; (2). −100 mV holding potential every 15 seconds pulse to −20 mV for 70 msec duration; the effectiveness of the drug in inhibiting the current mediated by the channel is measured directly from measuring the reduction in peak current amplitude initiated by the shift in potential from −100 mV to −20 mV. The difference in block at the two holding potentials was used to determine the effect of drug at differing levels of inactivation induced by the level of resting state potential of the cells. After obtaining control baseline calcium currents, extracellular solutions containing increasing concentrations of a test compound are washed in. Once steady state inhibition at a given compound concentration is reached, a higher concentration of compound is applied. % inhibition of the peak inward control Ca2+ current during the depolarizing step to −20 mV is plotted as a function of compound concentration.

The intrinsic T-type calcium channel antagonist activity of a compound which may be used in the present invention may be determined by these assays. In particular, the compounds of the following examples had activity in antagonizing the T-type calcium channel in the aforementioned assays, generally with an $IC_{50}$ of less than about 10 μM. Preferred compounds within the present invention had activity in antagonizing the T-type calcium channel in the aforementioned assays with an $IC_{50}$ of less than about 1 μM. Such a result is indicative of the intrinsic activity of the compounds in use as antagonists of T-type calcium channel activity.

With respect to the compounds disclosed in WO93/04047, WO 2004/035000, and DE 4320347 the present compounds exhibit unexpected properties, such as with respect to duration of action and/or metabolism, such as increased metabolic stability, enhanced oral bioavailability or absorption, and/or decreased drug-drug interactions.

T-type calcium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with calcium channels, including one or more of the following conditions or diseases: movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, seizure disorders, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); heart disease, abnormal heart rhythms and arrythmias, myocardial infarction, congestive heart failure, coronary heart disease, sudden death, stroke, sexual and reproductive dysfunction, such as impaired fertility, infertility, diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing trained performance; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing the amount of Delta sleep early in the sleep cycle, increasing REM sleep late in the sleep cycle; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, obstructive sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and graffing, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in preferred embodiments the present invention provides methods for: treating, controlling, ameliorating or reducing the risk of epilepsy, including absence epilepsy; treating or controlling Parkinson's disease; treating essential tremor; treating or controlling pain, including neuropathic pain; enhancing the quality of sleep; augmenting sleep maintenance; increasing REM sleep; increasing slow wave sleep; decreasing fragmentation of sleep patterns; treating insomnia; enhancing cognition; increasing memory retention; treating or controlling depression; treating or controlling psychosis; or treating, controlling, ameliorating or reducing the risk of schizophrenia, in a mammalian patient in need thereof which comprises administering to the patient a therapeutically effective amount of the compound of the present invention.

The subject compounds are further useful in a method for the prevention, treatment, control, amelioration, or reducation of risk of the diseases, disorders and conditions noted herein.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of T-type calcium channel. The dosage range will generally be about 0.5 mg to 1.0 g. per patient per day which may be administered in single or multiple doses. Preferably, the dosage range will be about 0.5 mg to 500 mg per patient per day; more preferably about 0.5 mg to 200 mg per patient per day; and even more preferably about 5 mg to 50 mg per patient per day. Pharmaceutical compositions of the present invention may be provided in a solid dosage formulation preferably comprising about 0.5 mg to 500 mg active ingredient, more preferably comprising about 1 mg to 250 mg active ingredient. The pharmaceutical composition is preferably provided in a solid dosage formulation comprising about 1 mg, 5 mg, 10 mg, 25 mg, 50 mg, 100 mg, 200 mg or 250 mg active ingredient. For oral administration, the compositions are preferably provided in the form of tablets containing 1.0 to 1000 milligrams of the active ingredient, particularly 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be employed in combination with an anti-seizure agent such as carbamazepine, clonazepam, divalproex, ethosuximide, felbamate, fosphenyloin, gabapentin, lamotrigine, levetiracetam, lorazepam, midazolam, oxcarbazepine, phenobarbital, phenyloin, primidone, tiagabine, topiramate, valproate, vigabatrin or zonisamide. In another embodiment, the subject compound may be employed in combination with acetophenazine, alentemol, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene, trifluoperazine or valproic acid.

In another embodiment, the compounds of the present invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compounds of the present invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the compounds of the present invention may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. In another embodiment, the subject compound may be employed in combination with an L-type calcium channel antagonist, such as amlodipine.

In another embodiment, the compounds of the present invention may be administered in combination with compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, other T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the compounds of the present invention may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the compounds of the present invention may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H$_3$ antagonists; AMPA agonists; PDE IV inhibitors; GABA$_A$ inverse agonists; or neuronal nicotinic agonists.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; BuLi: butyllithium; Piv: pivaloyl; Ac: acetyl; THF: tetrahydrofuran; DMSO: dimethylsulfoxide; EDC: N-(3-Dimethylaminopropyl)-N'-ethylcarbodiimide; Boc: tert-butyloxy carbonyl; $Et_3N$: triethylamine; DCM: dichloromethane; DCE: dichloroethane; DME: dimethoxyethane; DEA: diethylamine; DAST: diethylaminosulfur trifluoride; EtMgBr: ethylamgnesium bromide; BSA: bovine serum albumin; TFA: trifluoracetic acid; DMF: N,N-dimethylformamide; $SOCl_2$: thionyl chloride; CDI: carbonyl diimidazole; rt: room temperature; HPLC: high performance liquid chromatography. The compounds of the present invention can be prepared in a variety of fashions.

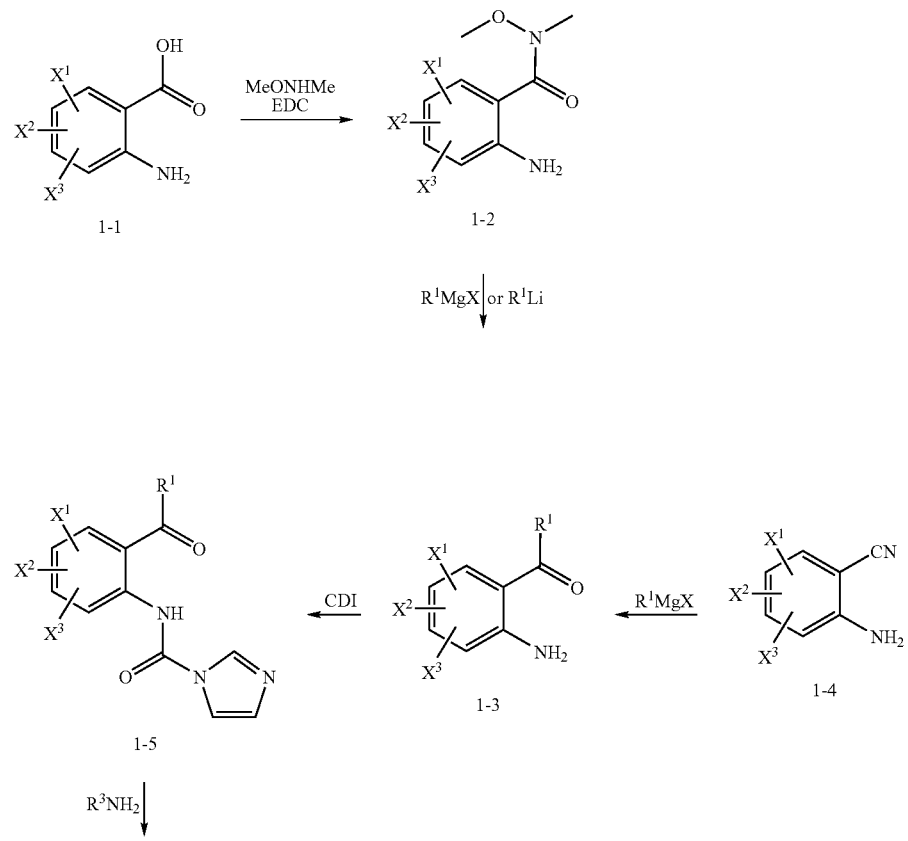

SCHEME 1

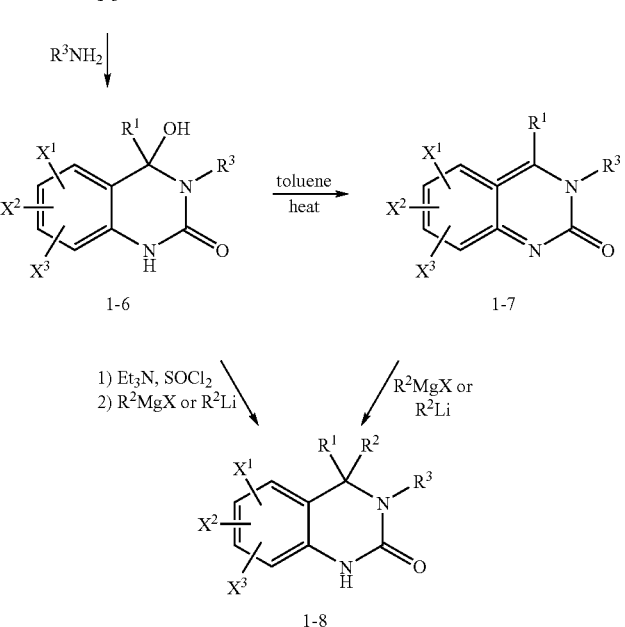

Treatment of an appropriately substituted 2-amino carboxylic acid 1-1 with N,O-dimethylhydroxylamine and a coupling reagent such as EDC gives the Weinreb amide 1-2. Addition of an organometallic reagent gives ketone 1-3 which can alternatively be prepared by addition of an organometallic reagent to an appropriately substituted nitrile 1-4. The ketone 1-3 can be elaborated to the imidazole adduct 1-5 with CDI. Treatment with the desired primary amine gives 1-6 (which can exist as mixture of the cyclized 4-hydroxyquinazolinone and the uncyclized keto-urea) which can be dehydrated to 1-7 and reacted with another organometallic to give compounds 1-8.

SCHEME 2

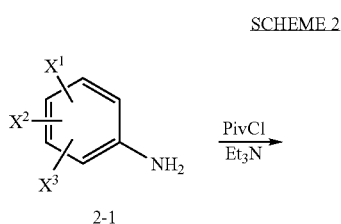

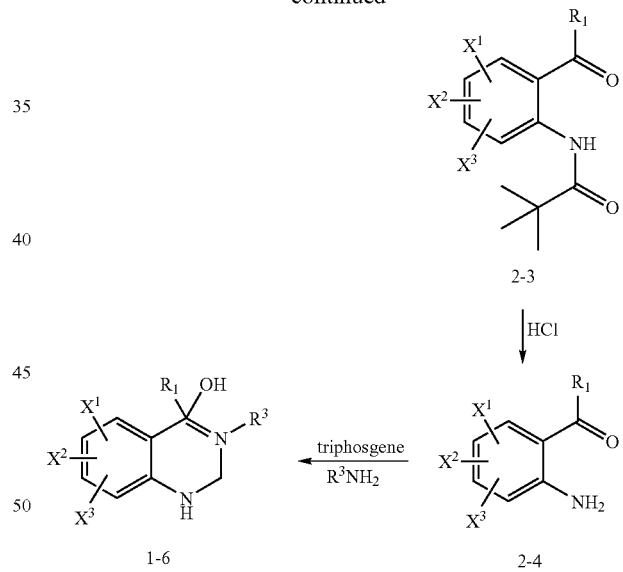

Another general method for preparation of hydroxyquinazolinone intermediate 1-6 is shown in Scheme 2. Protection of an appropriately substituted aniline 2-1 with pivaloyl chloride followed by directed ortho-metallation and trapping with an ester gives ketone 2-3. The pivaloyl group is removed with HCl and treatment of the resulting aminoketone 2-4 with triphosgene and an appropriately substituted amine gives 1-6 (which can exist as mixture of the cyclized 4-hydroxyquinazolinone and the uncyclized keto-urea).

In some cases the final product may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

EXAMPLE 1 vigorous stirring. The resulting precipitate was collected by vacuum filtration and placed under vacuum alongside P$_2$O$_5$ for 16 h to give 35.4 g (82.4%) of 6-chloro-4-hydroxy-4-phenyl-3-(2,2,2-trifluoroethyl)-3,4-dihydroquinazolin-2 (1H)-one as an off-white solid. 1H NMR (CDCl$_3$, 400 MHz) 8.41 (brs, 1H); 7.47 (d, J=8.06 Hz, 2H); 7.36 (m, 3H); 7.27 (m, 1H); 7.21 (dd, J=2.26 Hz and 8.52 Hz, 1H); 6.76 (d, J=8.52 Hz, 1H); 4.37 (m, 1H); 3.55 (m, 1H); 3.25 (s, 1H). MS (Electrospray): m/z 357.0 (M+H).

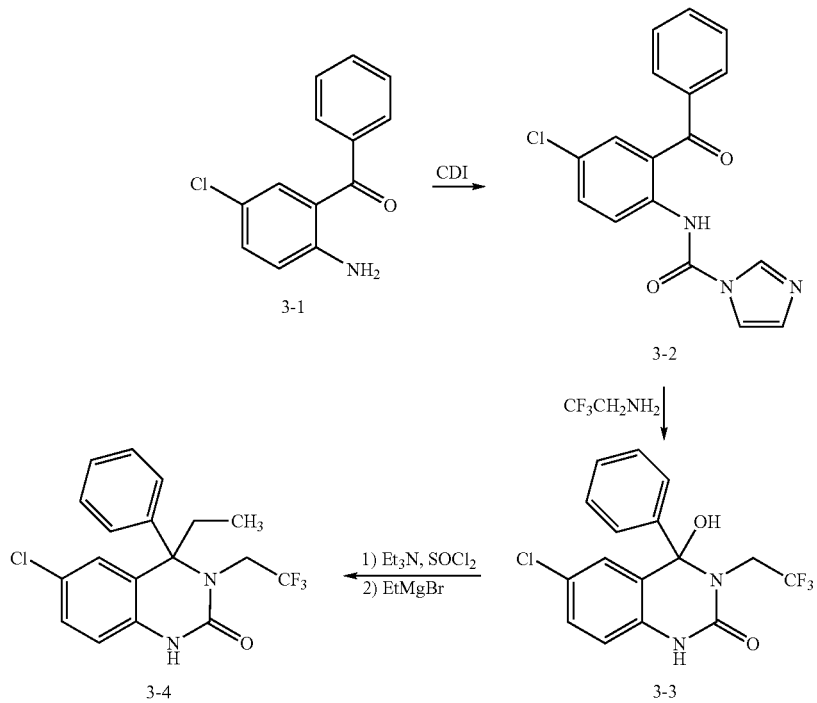

N-(2-benzoyl-4-chlorophenyl)-1H-imidazole-1-carboxamide (3-2)

To a solution of 2-amino-5-chlorobenzophenone (40 g, 172.7 mmol) in CH$_2$Cl$_2$ (175 μL) was added carbonyldiimidazole (30.8 g, 189.9 mmol). The reaction was heated to 45° C. for 16 h resulting in a white precipitate. The reaction was cooled in an ice bath and the precipitate collected by vacuum filtration and dried to give 39.3 g (69.9%) of N-(2-benzoyl-4-chlorophenyl)-1H-imidazole-1-carboxamide as a white solid. 1H NMR (CDCl$_3$, 400 MHz) 8.66 (s, 1H); 7.46 (m, 4H); 7.25 (s, 1H); 7.19 (d, J=6.96 Hz, 2H); 7.15 (s, 1H); 6.94 (m, 2H); 6.76 (d, J=2.29 Hz, 1H). MS (Electrospray): m/z 348.0 (M+Na).

6-chloro-4-hydroxy-4-phenyl-3-(2,2,2-trifluoroethyl)-3,4-dihydroquinazolin-2(1H)-one (3-3)

To a suspension of N-(2-benzoyl-4-chlorophenyl)-1H-imidazole-1-carboxamide (39.3 g, 120.5 mmol) in THF (200 mL) was added 2,2,2-trifluoroethylamine (14.0 g, 141.0 mmol). The reaction was heated to 50° C. for 16 h. A second portion of 2,2,2-trifluoroethylamine (3.6 gm, 36.4 mmol) was added and warming continued at 50° C. for 3 h. The reaction was cooled to ambient temperature and concentrated in vacuo. The light yellow oil was partitioned between n-butyl chloride (500 mL) and aqueous 10% citric acid (300 mL) with 4-ethyl-6-chloro-4-phenyl-3-(2,2,2-trifluoroethyl)-3,4-dihydroquinazolin-2(1H)-one (3-4)

To a −20° C. solution of 6-chloro-4-hydroxy-4-phenyl-3-(2,2,2-trifluoroethyl)-3,4-dihydroquinazolin-2(1H)-one (5.5 g, 15 mmol) in THF (50 mL) was added triethylamine (10.7 mL, 77 mmol) and then thionyl chloride (1.2 mL, 17 mmol) was added dropwise. After 20 min, 1M ethylmagnesium bromide in THF (46 mL, 46 mmol) was added over 10 min. and the reaction mixture warmed to 0° C. After an additional 30 min at 0° C., the reaction was quenched by pouring into a well stirred mixture of 300 mL EtOAc and 200 mL water which was acidified with 1N HCl solution. The layers were mixed and separated and the organic layer washed with 200 mL brine and filtered to remove unreacted starting material. The filtrate was concentrated in vacuo. Purification by normal phase chromatography (120 g silica gel cartridge, 10-75% EtOAc/hexanes) provided 4-ethyl-6-chloro-4-phenyl-3-(2,2,2-trifluoroethyl)-3,4-dihydroquinazolin-2(1H)-one. 1H NMR (CDCl$_3$, 400 MHz) δ 8.73 (s, NH); 7.39 (m, 3H); 7.35 (m, 2H); 7.09 (dd, 1H, J=8.43 and 2.2 Hz); 6.70 (d, 1H, J=8.43 Hz); 6.49 (d, 1H, J=2.38 Hz); 3.92 (dq, 1H, J=9.52 and 15.9 Hz); 3.47 (dq, 1H, J=8.61 and 17 Hz); 2.41 (dq, 1H, J=7.14 and 14.29 Hz); 2.28 (dq, 1H, J=7.14 and 14.28 Hz); 0.91 (t, J=7.14 Hz, 3H); MS (Electrospray): m/z 369.2 (M+H)

EXAMPLE 2

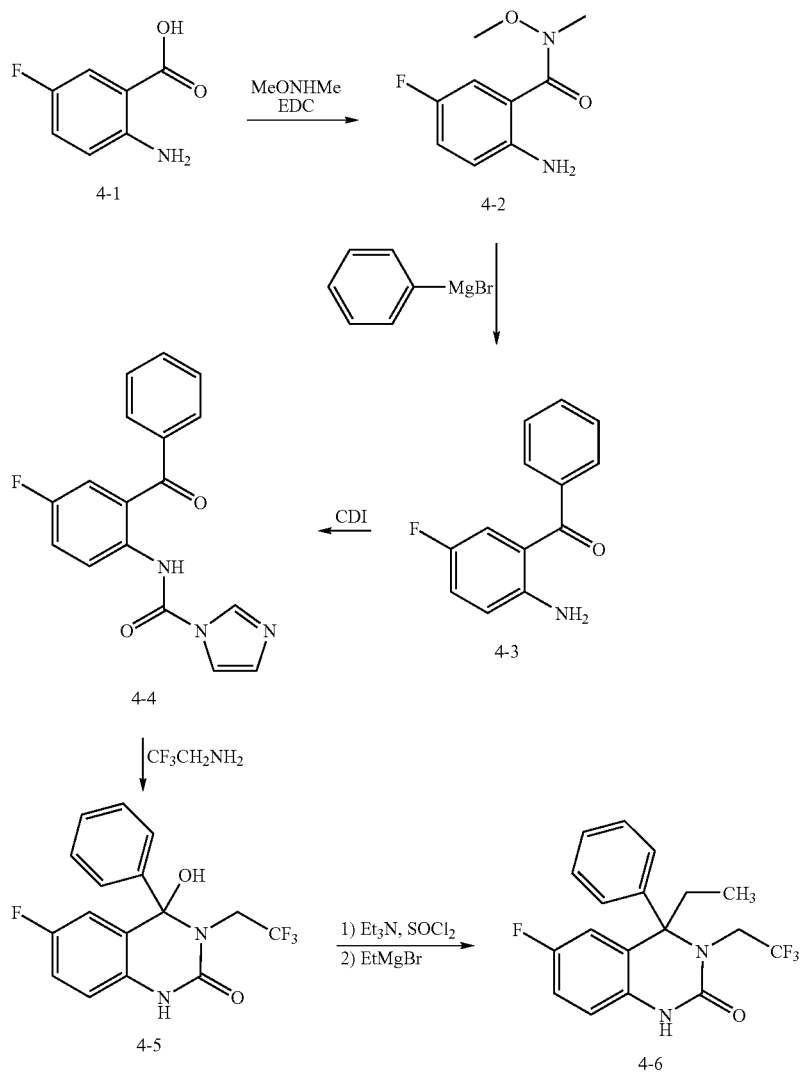

2-amino-5-fluoro-N-methoxy-N-methylbenzamide (4-2)

To a 0° C. mixture of diisopropylethylamine (34.36 mL, 197.25 mmol) and O,N-dimethyl-hydroxylamine hydrochloride (19.24 g, 197.25 mmol) in CHCl$_3$ (300 mL) was added 2-amino-5-fluorobenzoic acid (25.50 g, 164.38 mmol) followed by EDC (31.51 g, 164.38 mmol). The reaction was stirred from 0° C. to ambient temperature over 2 h and then diluted with CH$_2$Cl$_2$ (100 mL), washed with saturated sodium bicarbonate solution (100 mL) and brine (100 mL), dried over Na$_2$SO$_4$, filtered, and concentrated in vacuo. Purification by normal phase chromatography (3-8% MeOH/CH$_2$Cl$_2$) yielded 2-amino-5-fluoro-N-methoxy-N-methylbenzamide as a yellow oil. 1H NMR (CDCl$_3$, 400 MHz) 7.12 (m, 1H, ArH); 6.93 (m, 1H, ArH); 6.65 (m, 1H, ArH); 3.63 (s, 3H, CH$_3$); 3.35 (s, 3H, CH$_3$); MS (Electrospray): m/z 199.1 (M$^+$H).

(2-amino-5-fluorophenyl)(phenyl)methanone (4-3)

To a −78° C. solution of 2-amino-5-fluoro-N-methoxy-N-methylbenzamide in THF (100 mL) was added 1M phenylmagnesium bromide in THF (124.12 mL, 124.12 mmol). The reaction was stirred from −78° C. to ambient temperature over 3.5 h and then cooled again to −78° C. Additional 1M phenylmagnesium bromide in THF (62.06 mL, 62.06 mmol) was added and the reaction stirred at −78° C. for another hour. The reaction was then diluted with CH$_2$Cl$_2$ (500 mL) and quenched with saturated ammonium chloride solution (300 mL). The layers were separated and the organic one washed with brine (300 mL), dried over Na$_2$SO$_4$, filtered and concentrated in vacuo. Purification by normal phase chromatography (3-8% MeOH/CH$_2$Cl$_2$) yielded (2-amino-5-fluorophenyl)(phenyl)methanone as a yellow solid. 1H NMR (CDCl$_3$, 400 MHz) 7.63 (m, 2H, ArH); 7.55 (m, 1H, ArH); 7.47 (m, 2H, ArH); 7.15 (m, 1H, ArH); 7.08 (m, 1H, ArH); 6.70 (m, 1H, ArH); 5.91 (s, NH$_2$); MS (Electrospray): m/z 216.1 (M$^+$H).

N-(2-benzoyl-4-fluorophenyl)-1H-imidazole-1-carboxamide (4-4)

To a solution of (2-amino-5-fluorophenyl)(phenyl)methanone (6.60 g, 30.67 mmol) in CH$_2$Cl$_2$ (60 mL) was added carbonyldiimidazole (6.96 g, 42.93 mmol). The reaction was heated to 45° C. After 16 h at 45° C., the reaction was cooled to ambient temperature and the precipitate isolated by vacuum filtration and washed with fresh CH$_2$Cl$_2$ to give N-(2-benzoyl-4-fluorophenyl)-1H-imidazole-1-carboxamide as a white solid. 1H NMR (CDCl$_3$, 400 MHz) 8.91 (s, NH); 7.47 (m, 3H, ArH); 7.25 (m, 1H, ArH); 7.18 (m, 4H, ArH); 6.99 (m, 1H, ArH); 6.95 (s, 1H, ArH); 6.53 (m, 1H, ArH); MS (Electrospray): m/z 332.1 (M$^+$Na).

6-fluoro-4-hydroxy-4-phenyl-3-(2,2,2-trifluoroethyl)-3,4-dihydroquinazolin-2(1H)-one (4-5)

To a suspension of N-(2-benzoyl-4-fluorophenyl)-1H-imidazole-1-carboxamide (30.00 g, 97.00 mmol) in THF (300 mL) was added 2,2,2-trifluoroethylamine (11.53 g, 116.39 mmol). The reaction was heated to 50° C. After 19 h at 50° C., the reaction was cooled to ambient temperature. Butyl chloride (500 mL) and 10% citric acid (250 mL) were added and the reaction stirred vigorously for 40 min. The precipitate was then isolated by vacuum filtration and placed under vacuum alongside P$_2$O$_5$ for 16 h to give 6-fluoro-4-hydroxy-4-phenyl-3-(2,2,2-trifluoroethyl)-3,4-dihydroquinazolin-2(1H)-one as a yellow solid. 1H NMR (CDCl$_3$, 400 MHz) 8.59 (s, NH); d (7.47, J=6.96 Hz, 2H, ArH); 7.36 (m, 3H, ArH); 6.99 (m, 2H, ArH); 6.79 (m, 1H, ArH); 4.39 (m, 1H, CH$_2$); 3.56 (m, 1H, CH$_2$); 3.23 (s, OH); MS (Electrospray): m/z 363.0 (M$^+$Na).

(−)-4-ethyl-6-fluoro-4-phenyl-3-(2,2,2-trifluoroethyl)-3,4-dihydroquinazolin-2(1H)-one (4-6)

To a −15° C. solution of 6-fluoro-4-hydroxy-4-phenyl-3-(2,2,2-trifluoroethyl)-3,4-dihydroquinazolin-2(1H)-one (3.00 g, 8.82 mmol) in THF (40 mL) was added triethylamine (6.14 mL, 44.08 mmol). The reaction was stirred for a couple of minutes and then thionyl chloride (0.68 mL, 9.26 mmol) was added dropwise. After 25 min, 1M ethylmagnesium bromide in THF (27.33 mL, 27.33 mmol) was added over 10 min. After an additional 30 min at −15° C., the reaction was quenched with saturated ammonium chloride solution (60 mL) and extracted with CH$_2$Cl$_2$ (120 mL×2). The combined organics were washed with brine (60 mL), dried over dried over Na$_2$SO$_4$, filtered, and concentrated in vacuo. Purification by normal phase chromatography (0-70% EtOAc/hexanes) followed by chiral reverse phase chromatography (ChiralPak AD packing, 10-60% iPrOH/hexanes with DEA modifier) yielded a yellow residue that was taken up in a minimal amount of CH$_2$Cl$_2$, diluted with hexanes, and then concentrated in vacuo to give (−)-4-ethyl-6-fluoro-4-phenyl-3-(2,2,2-trifluoroethyl)-3,4-dihydroquinazolin-2(1H)-one. 1H NMR (CDCl$_3$, 400 MHz) 8.26 (s, NH); 7.38 (m, 5H, ArH); 6.85 (m, 1H, ArH); 6.70 (m, 1H, ArH); 6.25 (m, 1H, ArH); 3.92 (m, 1H, CH$_2$); 3.48 (m, 1H, CH$_2$); 2.35 (m, 2H, CH$_2$); 0.91 (t, J=6.87 Hz, 3H, CH$_3$); MS (Electrospray): m/z 353.1292 (M$^+$H); [α]$_D$=−41.8° (c0.11, MeOH). For the (+)-enantiomer, [α]$_D$=+41.1° (c0.12, MeOH).

EXAMPLE 3

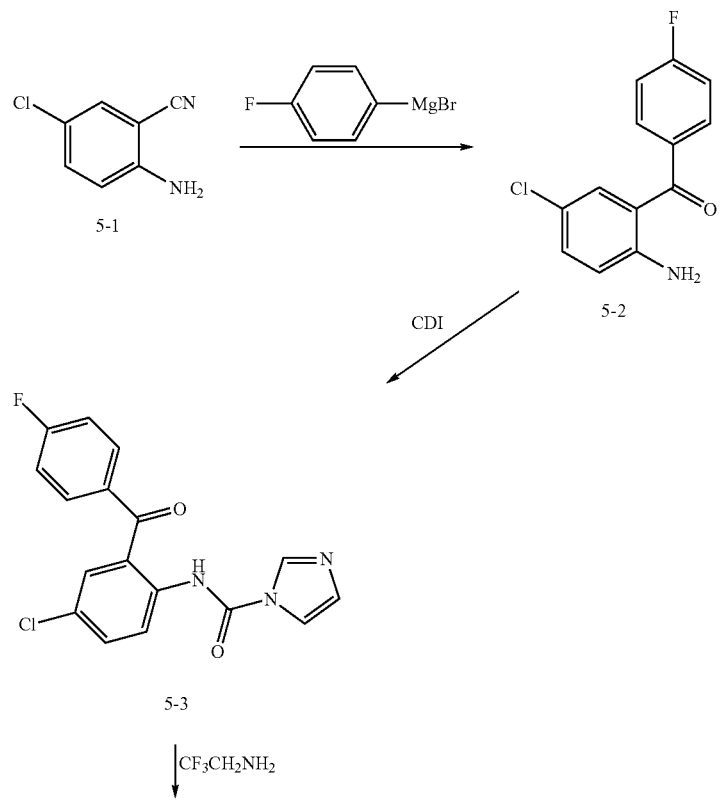

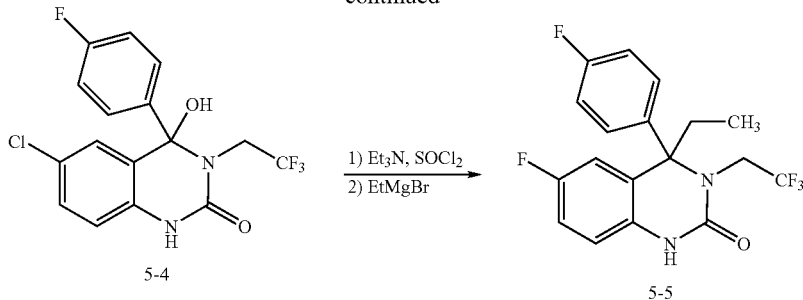

(2-Amino-5-chlorophenyl)(4-fluorophenyl)methanone (5-1)

To a 0° C. solution of 1.0M 4-fluorophenylmagnesium bromide in THF (196.6 mL, 196.6 mmol) was added a THF solution (100 mL) of 2-amino-5-chlorobenzonitrile (10.0 gm, 65.5 mmol) over 0.5 h. The ice bath was removed and the reaction stirred at ambient temperature for 17 h. The brown solution was cooled in an ice bath, treated with a drop wise addition of aqueous 1N HCl (300 mL) and extracted with ether (2×250 mL). The combined organic extracts were washed with aqueous 1N HCl (100 mL), water (2×150 ml), saturated aqueous sodium bicarbonate (150 ml), brine (100 mL), dried over $MgSO_4$, filtered, concentrated in vacuo to 30 mL and diluted with 60 mL hexane. The resulting precipitate was filtered to give (2-amino-5-chlorophenyl)(4-fluorophenyl)methanone as a yellow solid.

1H NMR ($CDCl_3$, 400 MHz) 7.67 (m, 2H); 7.37 (d, J=2.38 Hz, 1H); 7.25 (m, 1H); 7.16 (m, 2H); 6.70 (d, J=8.79 Hz, 1H); 5.99 (s). MS (Electrospray): m/z 250.1 (M+H).

N-[4-chloro-2-(4-fluorobenzoyl)phenyl]-1H-imidazole-1-carboxamide (5-2)

To a solution of (2-amino-5-chlorophenyl)(phenyl)methanone (50.1 g, 200.7 mmol) in $CH_2Cl_2$ (500 mL) was added carbonyldiimidazole (35.8 g, 220.7 mmol). The reaction was heated to 45° C. for 16 h. Additional carbonyldiimidazole (9.8 g, 60.2 mmol) was added and heating continued at 45° C. for 6 h. The reaction was concentrated in vacuo and the crude foam partitioned between methyl-tert-butylether (400 mL) and water (100 mL) with vigorous stirring. The resulting precipitate was collected by vacuum filtration and washed with fresh water, followed by methyl-tert-butylether and heptane to give N-[4-chloro-2-(4-fluorobenzoyl)phenyl]-1H-imidazole-1-carboxamide as an off-white solid. 1H NMR ($d_6$-DMSO, 400 MHz) 11.06 (s); 7.58 (m, 1H); 7.36 (m, 3H); 7.23 (m, 2H); 7.08 (m, 3H); 6.74 (s, 1H). MS (Electrospray): m/z 366.0 (M+Na).

6-chloro-4-(4-fluorophenyl-4-hydroxy-3-(2,2,2-trifluoroethyl)-3,4-dihydroquinazolin-2(1H)-one (5-3)

To a suspension of N-[4-chloro-2-(4-fluorobenzoyl)phenyl]-1H-imidazole-1-carboxamide (63.0 g, 183.3 mmol) in THF (315 mL) was added 2,2,2-trifluoroethylamine (24.5 g, 247.4 mmol). The reaction was heated to 50° C. After 19 h at 50° C., the reaction was cooled to ambient temperature and concentrated in vacuo. The light yellow oil was partitioned between n-butyl chloride (110 mL) and aqueous 10% citric acid (60 mL) with vigorous stirring. The resulting precipitate was collected by vacuum filtration and placed under vacuum alongside $P_2O_5$ for 16 h to give 6-chloro-4-(4-fluorophenyl)-4-hydroxy-3-(2,2,2-trifluoroethyl)-3,4-dihydroquinazolin-2 (1H)-one as an off-white solid.

1H NMR ($d_6$-DMSO, 400 MHz) 10.32 (s); 7.73 (s, 1H); 7.41 (m, 2H); 7.27 (dd, J=2.38 Hz and 8.61 Hz, 1H); 7.20 (m, 2H); 6.97 (d, J=2.38 Hz, 1H); 6.92 (d, J=8.61 Hz, 1H); 4.13 (m, 1H); 3.64 (m, 1H); 3.32 (s). MS (Electrospray): m/z 357.1 (M+H–$H_2O$).

6-chloro-4-ethyl-4-(4-fluorophenyl)-3-(2,2,2-trifluoroethyl)-3,4-dihydroquinazolin-2(1H)-one (54)

To a −15° C. solution of 6-chloro-4-(4-fluorophenyl)-4-hydroxy-3-(2,2,2-trifluoroethyl)-3,4-dihydroquinazolin-2 (1H)-one (6.20 g, 16.5 mmol) in anhydrous toluene (60 mL) was added triethylamine (11.5 mL, 82.7 mmol). The reaction was stirred for 5 min and then thionyl chloride (1.27 mL, 17.4 mmol) was added dropwise maintaining the temperature < −5° C. After 15 min, 1M ethylmagnesium bromide in THF (51.3 mL, 51.3 mmol) was added over 35 min maintaining the temperature <−5° C. The reaction was warmed from −15° C. to 0° C. over 30 min and then poured into a vigorously stirred mixture of aqueous 10% citric acid (30 mL), ice (30 g), and ethyl acetate (50 mL). The aqueous phase was extracted with ethyl acetate (3×50 mL). The combined organics were washed with water (50 mL), brine (60 mL), dried over $Na_2SO_4$, filtered, and concentrated in vacuo. Purification by normal phase chromatography (0-25% EtOAc/hexanes) gave a crude light yellow oil. Crystallization of the oil from hexane gave racemic 6-chloro-4-ethyl-4-(4-fluorophenyl)-3-(2,2,2-trifluoroethyl)-3,4-dihydroquinazolin-2(1H)-one as an off-white solid. 1H NMR ($CDCl_3$, 400 MHz) 8.19 (s, NH); 7.39 (m, 2H, ArH); 7.09 (m, 3H, ArH); 6.68 (d, J=8.51 Hz, 1H, ArH); 6.46 (d, J=2.11 Hz, 1H, ArH); 3.84 (m, 1H, $CH_2$); 3.56 (m, 1H, $CH_2$); 2.40 (m, 1H, $CH_2$); 2.22 (m, 1H, $CH_2$); 0.90 (t, J=7.15 Hz, 3H, $CH_3$); MS (Electrospray): m/z 387.1 ($M^+H$). Racemic 6-chloro-4-ethyl-4-(4-fluorophenyl)-3-(2,2,2-trifluoroethyl)-3,4-dihydroquinazolin-2(1H)-one (2.76 g) was resolved using chiral reverse phase chromatography (ChiralPak AD packing, 10-30% iPrOH/hexanes with DEA modifier at 1.0 mL/L). The enantiomers were obtained as crystalline solids from hexane to give (+) compound as Peak 1 and (−) compound as Peak 2. Data for Peak 2: 1H NMR ($CDCl_3$, 400 MHz) 8.69 (s, NH); 7.39 (m, 2H, ArH); 7.09 (m, 3H, ArH); 6.70 (d, J=8.60 Hz, 1H, ArH); 6.45 (d, J=2.20 Hz, 1H, ArH); 3.81 (m, 1H, $CH_2$); 3.59 (m, 1H, $CH_2$); 2.40 (m, 1H, $CH_2$); 2.22 (m, 1H, $CH_2$); 0.90 (t, J=7.14 Hz, 3H, $CH_3$); MS (Electrospray): m/z 387.0894 ($M^+H$); $[\alpha]_D$=−8.5° (c0.0024, $CH_2Cl_2$). Data for Peak 1, the (+)-enantiomer, $[\alpha]_D$=+7.9° (c0.0027, $CH_2Cl_2$).

EXAMPLE 4

4-Allyl-6-chloro-4-(4-fluorophenyl)-3-(2,2,2-trifluoroethyl)-3,4-dihydroquinazolin-2(1H)-one To a −40° C. solution of 6-chloro-4-(4-fluorophenyl)-4-hydroxy-3-(2,2,2-trifluoroethyl)-3,4-dihydroquinazolin-2(1H)-one (21.2 g, 56.6 mmol) in anhydrous THF (170 mL) was added triethylamine (39.4 mL, 283 mmol). The reaction was stirred for 5 min and then thionyl chloride (4.4 mL, 59.4 mmol) was added drop wise maintaining the temperature < −20° C. After 25 min, 1.0M allylmagnesium bromide in THF (170 mL, 170 mmol) was added over 35 min maintaining the temperature <−10° C. The reaction was stirred <−5° C. over 30 min and then poured into a vigorously stirred mixture of aqueous 10% citric acid (150 mL), ice (50 g), and ethyl acetate (200 mL). The aqueous phase was extracted with ethyl acetate (3×100 mL). The combined organics were washed with water (100 mL), brine (100 mL), dried over $Na_2SO_4$, filtered, and concentrated in vacuo to give a crude brown oil. The oil was dissolved in methylene chloride (100 mL) and stirred 1 hr. The resulting precipitate was collected by vacuum filtration and dried under vacuum for 16 h to give racemic 4-allyl-6-chloro-4-(4-fluorophenyl)-3-(2,2,2-trifluoroethyl)-3,4-dihydroquinazolin-2(1H)-one as an off-white solid.

1H NMR ($d_6$-DMSO, 400 MHz) 9.98 (s, 1H); 7.46 (m, 2H); 7.21 (m, 3H); 6.83 (d, J=8.61 Hz, 1H); 6.54 (d, J=2.01 Hz, 1H); 5.47 (m, 1H); 5.10 (m, 2H); 4.03 (m, 1H); 3.73 (m, 1H); 3.29 (m, 1H); 3.01 (m, 1H). MS (Electrospray): m/z 399.0 (M+H).

EXAMPLE 5

(−)-6-Chloro-4-(4-fluorophenyl)-4-propyl-3-(2,2,2-trifluoroethyl)-3,4-dihydroquinazolin-2(1H)-one To a solution of 4-allyl-6-chloro-4-(4-fluorophenyl)-3-(2,2,2-trifluoroethyl)-3,4-dihydroquinazolin-2(1H)-one (22.1 g, 55.4 mmol) in ethyl acetate (450 mL) and under a nitrogen atmosphere was added 10% palladium on carbon (224 mg). A balloon of hydrogen was bubbled into the stirring mixture. The reaction was then stirred over night under an atmosphere of hydrogen. The reaction was purged with nitrogen, filtered through a pad of celite and the filtrate concentrated in vacuo to give 22.3 gm (100%) of (±)-6-chloro-4-(4-fluorophenyl)-4-propyl-3-(2,2,2-trifluoroethyl)-3,4-dihydroquinazolin-2(1H)-one as a white solid. Further purification by chiral chromatography (ChiralPak AD packing, 30% iPrOH/heptane with DEA modifier at 1.0 mL/L) followed by crystallization from hexanes provided individual enantiomers of 6-chloro-4-(4-fluorophenyl)-4-propyl-3-(2,2,2-trifluoroethyl)-3,4-dihydroquinazolin-2(1H)-one (Peak 1 and Peak 2). Data for Peak 2: 1H NMR ($d_6$-DMSO, 400 MHz) δ 10.02 (s, 1H); 7.43 (m, 2H); 7.20 (m, 3H); 6.84 (d, J=8.61 Hz, 1H); 6.59 (d, J=2.19 Hz, 1H); 3.80 (q, J=9.34 Hz, 2H); 2.33 (m, 2H); 1.24 (m, 1H); 0.94 (m, 1H); 0.89 (t, J=6.87 Hz, 3H). Exact Mass (Electrospray, M+H): Calc'd, 401.1039; Found, 401.1040. $[\alpha]_D$=−6.7° (c0.0045, MeOH). Optical rotation for Peak 1: $[\alpha]_D$=+5.2° (c0.0062, MeOH).

EXAMPLE 6

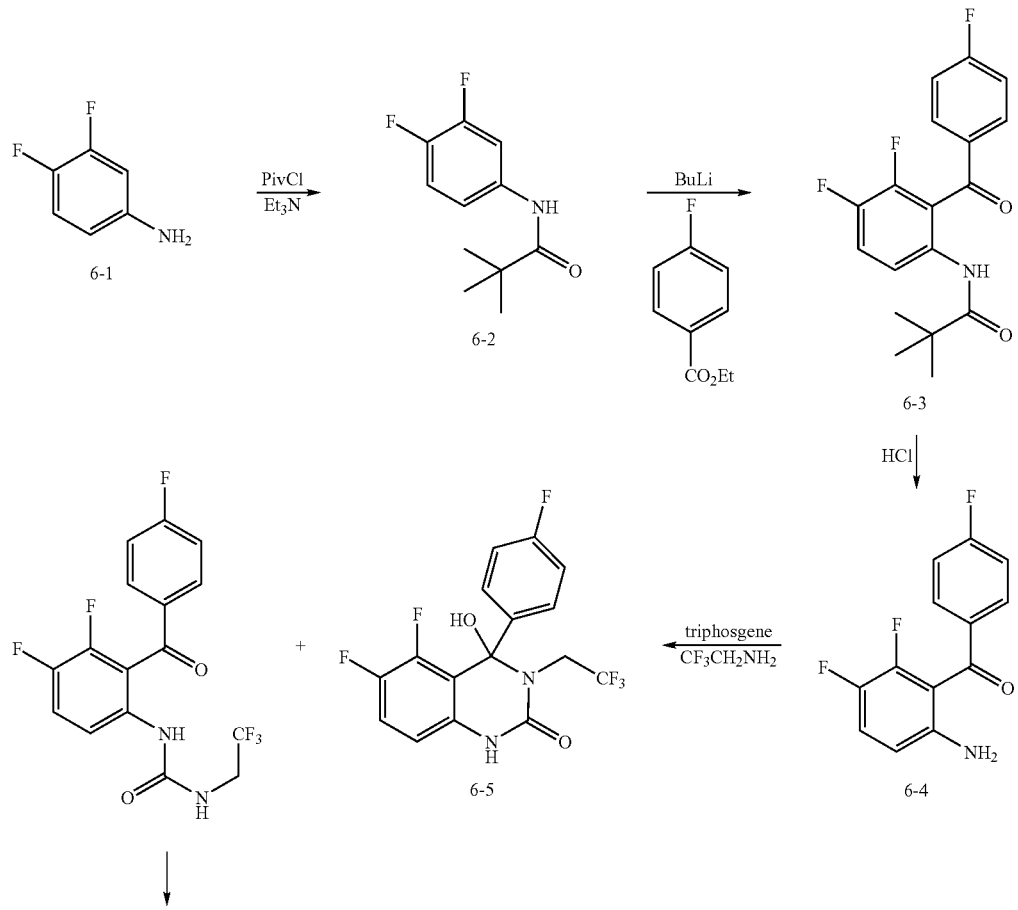

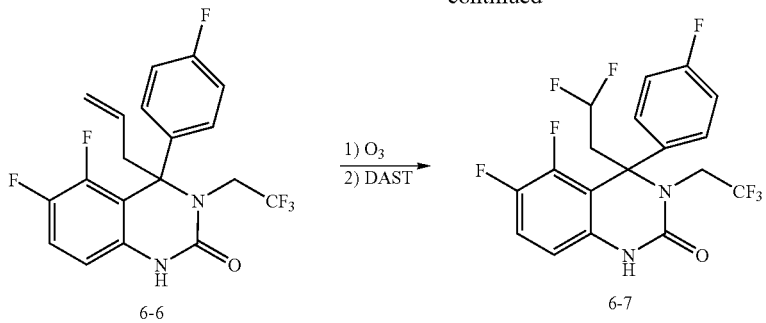

N-(3,4-Difluorophenyl)-2,2-dimethylpropanamide (6-2)

To a 0° C. solution of 5.250 g (40.663 mmol) 3,4-difluoroanailine in 75 ml dichloromethane was added 5.487 mL (44.729 mmol) pivaloyl chloride and 6.8 mL (48.796 mmol) triethylamine. After stirring 1 h from 0° C. to room temperature, the reaction mixture was diluted with $CH_2Cl_2$, washed with water and brine. The organic layer was dried over $NaSO_4$, filtered and concentrated in vacuo to afforded N-(3, 4-difluorophenyl)-2,2-dimethylpropanamide. $^1H$ NMR ($CDCl_3$, 400 MHz) δ 7.68-7.63 (m, 1H, ArH); 7.09-7.06 (m, 2H, ArH); 1.31 (s, 9H, O=C($CH_3$)$_3$). ES MS+1=214.1.

(6-amino-2,3-difluorophenyl)(4-fluorophenyl)methanone (6-4)

To a −78° C. solution of 2.5 g (11.724 mmol) N-(3,4-difluorophenyl)-2,2-dimethylpropanamide in 39 ml anhydrous THF was added drop wise over 15 mins 18 mL (28.136 mmol) n-BuLi (1.6M solution in cyclohexanes). After 1 hr at −78° C., 4 mL (26.966 mmol) ethyl 4-fluorobenzoate was added dropwise and the reaction mixture stirred from −78° C. to rt. After 45 mins, the reaction mixture was cooled to 0 C and quenched with saturated ammonium chloride and poured into a 1:1 mixture of ether:water and warmed to room temperature. The organic phase was isolated, washed with brine, dried over $MgSO_4$, filtered, and concentrated in vacuo to yield N-[3,4-difluoro-2-(4-fluorobenzoyl)phenyl]-2,2-dimethylpropanamide (6-3). A solution of 3.5 g (10.706 mmol) N-[3, 4-difluoro-2-(4-fluorobenzoyl)phenyl]-2,2-dimethylpropanamide in 43 mL 6N HCl and 8.6 mL DME was heated to 100° C. After 24 h at 100° C., the reaction mixture was cooled to room temperature and sodium carbonate was added until reaction mixture was basic. The reactions was diluted with water, extracted three times with ether, and washed with brine. The organic layer was dried over $MgSO_4$, filtered and concentrated in vacuo. Purification by flash chromatography (1×14 cm silica gel, linear gradient 0-20% EtOAc:hexane) afforded (6-amino-2,3-difluorophenyl)(4-fluorophenyl) methanone. $^1H$ NMR ($CDCl_3$, 400 MHz) δ 7.85-7.80 (m, 2H, ArH); 7.17-7.11 (m, 3H, ArH); 6.47 (ddd, J=2.01 Hz, 3.66 Hz, 9.16 Hz, 1H, ArH); 4.84 (br s, 2H, $ArNH_2$). ES MS+1=252.1.

N-[3,4-difluoro-2-(4-fluorobenzoyl)phenyl]-N'-(2,2,2-trifluoroethyl)urea (open form) and 5,6-difluoro-4-(4-fluorophenyl)-4-hydroxy-3-(2,2,2-trifluoroethyl)-3,4-dihydroquinazolin-2(1H)-one (closed form (6-5)

To a 0° C. solution of 0.85 g (2.89 mmol) triphosgene in 0.5 ml ether was slowly added a solution of 2.2 g (8.76 mmol) (6-amino-2,3-difluorophenyl)(4-fluorophenyl)methanone and 1.221 mL (8.758 mmol) triethylamine in 17.5 mL ether. After 1 h at 0° C., a solution of 0.7 mL (8.758 mmol) trifluoroethylamine and 1.221 mL (8.758 mmol) triethylamine in 17.5 mL ether was added quickly to the reaction mixture. The mixture was warmed to room temperature and after 5 h at room temperature, the reaction mixture was diluted with EtOAc, washed with saturated $NaHCO_3$ solution and brine. The organic layer was dried over $NaSO_4$, filtered and concentrated in vacuo. Added $CH_2Cl_2$ and isolated 0.740 g of white ppt. Concentrate filtrate and purify by flash chromatography (1×14 cm silica gel, linear gradient 0-50% EtOAc:hexane) afforded 0.7490 g. Isolated a total of 1.461 g (44%) of a 2:1.6 mixture of N-[3,4-difluoro-2-(4-fluorobenzoyl)phenyl]-N'-(2,2,2-trifluoroethyl)urea (close form) and 5,6-difluoro-4-(4-fluorophenyl)-4-hydroxy-3-(2,2,2-trifluoroethyl)-3,4-dihydroquinazolin-2(1H)-one (open form). Closed form $^1H$ NMR ($CDCl_3$, 400 MHz) δ 8.50 (br s, 1H, ArNHC=O); 7.50 (dd, J=5.31 Hz, 8.79 Hz, 2H, ArH); 7.13 (q, J=8.97 Hz, 17.03 Hz, 1H, ArH); 7.06 (t, J=8.61 Hz, 2H, ArH); 6.60-6.57 (m, 1H, ArH); 4.33-4.23 (m, 1H, $NCH_2CF_3$); 3.56-3.44 (m, 1H, $NCH_2CF_3$). Open form $^1H$ NMR ($CDCl_3$, 400 MHz) δ 8.34 (br s, 0.8H, ArNHC=O); 7.98-7.95 (m, 0.8H, ArH); 7.84 (td, J=1.65 Hz, 5.49 Hz, 1.6H, ArH); 7.35 (q, J=9.15 Hz, 18.31 Hz, 0.8H, ArH); 7.18 (t, J=8.42 Hz, 0.8H, ArH), 5.26 (br s, 0.8H, O=CNH$CH_2CF_3$); 3.94-384 (m, 1.6H, $NCH_2CF_3$).

4-Allyl-5,6-difluoro-4-(4-fluorophenyl)-3-(2,2,2-trifluoroethyl)-3,4-dihydroquinazolin-2(1H)-one (6-6)

To a solution of 5.0 g (13.289 mmol) N-[3,4-difluoro-2-(4-fluorobenzoyl)phenyl]-N'-(2,2,2-trifluoroethyl)urea (open form) and 5,6-difluoro-4-(4-fluorophenyl)-4-hydroxy-3-(2, 2,2-trifluoroethyl)-3,4-dihydroquinazolin-2(1H)-one (closed form) in 25 ml THF was added 9.261 mL (66.443 mmol) triethylamine. After 1 h at 80° C., the reaction mixture was cooled to −78° C. To this solution was added 0.969 mL (13.289 mmol) thionyl chloride. After 30 mins at −78° C., 45 mL (41.195 mmol) allylmagnesium bromide (1.0M solution in dibutyl ether) was added dropwise. After 30 minutes at −78° C., the reaction mixture was quenched with saturated $NH_4Cl$ and warmed to room temperature. The reaction mixture was extracted three times with EtOAc and washed with brine. The organic layer was dried over $NaSO_4$, filtered and concentrated in vacuo. Purification by flash chromatography (1×14 cm silica gel, linear gradient 0-35% EtOAc:hexane) afforded 4-allyl-5,6-difluoro-4-(4-fluorophenyl)-3-(2,2,2-trifluoroethyl)-3,4-dihydroquinazolin-2(1H)-one. 1H NMR ($CDCl_3$, 400 MHz) δ 7.46 (br s, 1H, ArNHC=O); 7.42-7.40 (m, 2H, ArH); 7.10-7.00 (m, 3H, ArH); 6.44 (m, 1H, ArH);

5.73-5.66 (m, 1H, CH2CH=CH2); 5.13-5.09 (m, 2H, CH2CH=CH2); 3.73 (m, 2H, NCH2CF3); 3.15 (m, 2H, CH2CH=CH2). HRMS (ES) exact mass calcd for $C_{19}H_{14}F_6N_2O$: 401.1083, Found: 401.1075.

EXAMPLE 7

[5,6-Difluoro-4-(4-fluorophenyl)-2-oxo-3-(2,2,2-trifluoroethyl)-1,2,3,4-tetrahydroquinazolin-4-yl]acetaldehyde To a −78° C. solution of 2.6 g (6.495 mmol) 4-allyl-5,6-difluoro-4-(4-fluorophenyl)-3-(2,2,2-trifluoroethyl)-3,4-dihydroquinazolin-2(1H)-one in 25 ml MeOH was bubbled ozone. After 15 mins at −78° C., the ozone was removed and the reaction mixture was quenched with 4.8 mL (64.946 mmol) dimethyl sulfide. After stirring at room temperature overnight, the reaction mixture was diluted with EtOAc and washed three times with water and brine. The organic layer was dried over $NaSO_4$, filtered and concentrated in vacuo. Afforded [5,6-difluoro-4-(4-fluorophenyl)-2-oxo-3-(2,2,2-trifluoroethyl)-1,2,3,4-tetrahydroquinazolin-4-yl]acetaldehyde. 1H NMR (CDCl$_3$, 400 MHz) δ 9.79 (s, 1H, O=CH); 8.61 (br s, 1H, ArNHC=O); 7.38-7.27 (m, 2H, ArH); 7.15-7.03 (m, 3H, ArH); 6.57-6.53 (m, 1H, ArH); 4.08 (m, 1H, C); 3.72 (dd, 1H, J=17.4 Hz, CH2C=O); 3.50 (dd, 1H J=1.28 Hz, 17.58 Hz, CH2C=O); 3.32 (m, 1H, CH2C=O). ES MS+1=403.1.

EXAMPLE 8

4-(2,2-Difluoroethyl)-5,6-difluoro-4-(4-fluorophenyl)-3-(2,2,2-trifluoroethyl)-3,4-dihydroquinazolin-2(1H)-one (6-7)

To a 0° C. solution of 2.4 g (5.966 mmol) [5,6-difluoro-4-(4-fluorophenyl)-2-oxo-3-(2,2,2-trifluoroethyl)-1,2,3,4-tetrahydroquinazolin-4-yl]acetaldehyde in 15 ml CH$_2$Cl$_2$ was added 2.192 mL (17.897 mmol) DAST reagent. After 30 min at 0° C., the reaction mixture was poured onto ice and warmed to room temperature. The reaction mixture was extracted three times with CH$_2$Cl$_2$ and washed with brine. The organic layer was dried over NaSO$_4$, filtered and concentrated in vacuo. Purification by flash chromatography (1×14 cm silica gel, linear gradient 0-40% EtOAc:hexane) afforded 4-(2,2-difluoroethyl)-5,6-difluoro-4-(4-fluorophenyl)-3-(2,2,2-trifluoroethyl)-3,4-dihydroquinazolin-2(1H)-one. Chiral separation (ChiralPak AD, 5 cm×50 cm, 20μ, 1:1 Hexanes/EtOH, modifier: DEA 1 mL/L, Flow: 50 mL/min, 30 mins) afforded the second peak off chiral column. 1H NMR (CDCl$_3$, 400 MHz) δ 8.87 (s, 1H, ArNHC=O); 7.39-7.35 (m, 2H, ArH); 7.14-7.07 (m, 3H, ArH); 6.59-6.55 (m, 1H, ArH); 6.03 (t, 0.25H, J=4.22 Hz, CH2CHF2); 5.89 (t, 0.50H J=4.40 Hz, CH2CHF2); 5.76 (t, 0.25H, CH2CHF2); 3.82 (m, 1H, NCH2CF3); 3.63 (m, 1H, NCH2CF3); 3.10 (m, 1H, CH2CHF2); 2.93 (m, 1H, CH2CHF2).

HRMS (ES) exact mass calcd for $C_{18}H_{12}F_8N_2O$: 425.0895, Found: 425.0880.

EXAMPLE 9

4-Ethyl-5,6-difluoro-4-(4-fluorophenyl)-3-(2,2,2-trifluoroethyl)-3,4-dihydroquinazolin-2(1H)-one To a solution of 1.5 g (3.987 mmol) N-[3,4-difluoro-2-(4-fluorobenzoyl)phenyl]-N'-(2,2,2-trifluoroethyl)urea (open form) and 5,6-difluoro-4-(4-fluorophenyl)-4-hydroxy-3-(2,2,2-trifluoroethyl)-3,4-dihydroquinazolin-2(1H)-one (closed form) in 8 ml THF was added 2.0 mL (19.933 mmol) triethylamine. After 1 h at 80° C., the reaction mixture was cooled to −78° C. To this solution was added 0.498 mL (4.186 mmol) thionyl chloride. After 30 minutes at −78° C., 5 mL (12.358 mmol) ethylmagnesium bromide (3.0M solution in diethyl ether) was added dropwise. After 1 h at −78° C., the reaction mixture was quenched with saturated NH$_4$Cl and warmed to room temperature. The reaction mixture was extracted three times with EtOAc and washed with brine. The organic layer was dried over NaSO$_4$, filtered and concentrated in vacuo. Purification by flash chromatography (1×14 cm silica gel, linear gradient 0-50% EtOAc:hexane) afforded 4-ethyl-5,6-difluoro-4-(4-fluorophenyl)-3-(2,2,2-trifluoroethyl)-3,4-dihydroquinazolin-2(1H)-one. Chiral Separation (ChiralPak AD column, 5 cm×50 cm, 20μ, 10-40% ethanol/hexane, modifier: DEA 1 mL/L, 60 mins) afforded 350 mg of the second isomer.

$[α]^{23}D$+0.464° (c=1.23, CH$_2$Cl$_2$); $^1$H NMR (CDCl$_3$, 400 MHz) δ 8.70 (br s, 1H, ArNHC=O); 7.40 (dd, 2H, J=5.13 Hz, 8.79 Hz, ArH); 7.09-7.00 (m, 3H, ArCH); 6.53-6.50 (m, 1H, ArH); 3.84 (m, 1H, NCH$_2$CF$_3$); 3.50 (m, 1H, NCH$_2$CF$_3$); 2.56 (m, 1H, CH$_2$CH$_3$); 2.36 (m, 1H, CH$_2$CH$_3$); 0.943 (t, 3H, J=7.14 Hz, CH$_2$CH$_3$). HRMS (ES) exact mass calcd for $C_{18}H_{14}F_6N_2O$ 389.1083, Found: 389.1063

EXAMPLE 10

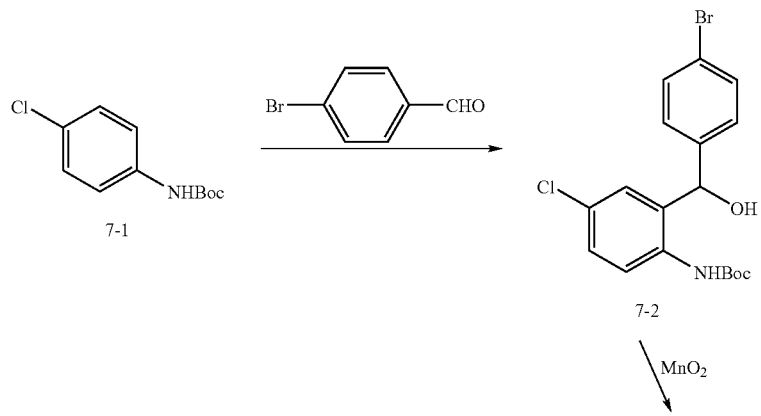

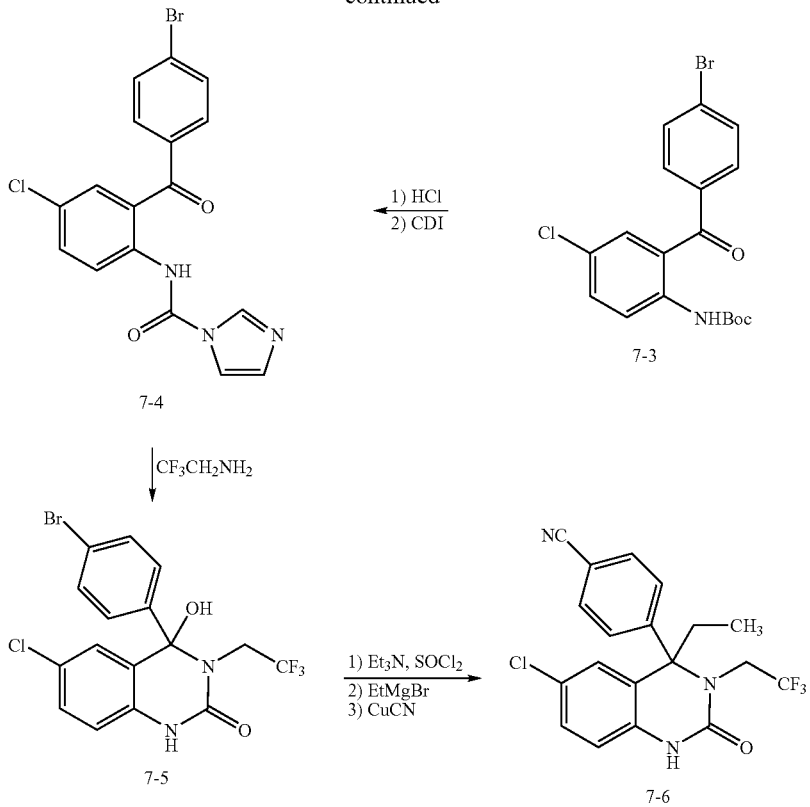

Tert-butyl {2-[(4-bromophenyl)(hydroxy)methyl]-4-chlorophenyl}carbamate (7-2)

To a −78° C. solution of tert-butyl (4-chlorophenyl)carbamate (3.0 g, 13.2 mmol) in 100 ml of THF was added TMEDA (1.53 g, 13.2 mmol) followed by sec-BuLi (21 ml, 32.9 mmol) slowly and dropwise via syringe. The reaction mixture turns bright yellow after about half the s-BuLi was added. The reaction mixture was allowed to stir for 15 min at −78° C. then allowed to warm to about −20° C. (tip of flask in dry-ice bath) for 1 hr, then the reaction mixture was cooled to −78° C. again. The reaction mixture was in now a dull yellow/orange, slightly heterogeneous and 4-bromobenzaldehyde was added dropwise, and stirred for 30 min at −78° C. The reaction mixture was quenched with 100 mL sat NH$_4$Cl (pink fades to yellow), extracted with 150 ml of ether, washed with brine, dried over MgSO$_4$, filtered and concentrated. The crude product was purified by silica gel chromatography using 5-30% EtOAc/hex as the eluent to provide tert-butyl {2-[(4-bromophenyl)(hydroxy)methyl]-4-chlorophenyl}carbamate as a yellow solid. $^1$HNMR: (400 MHz, CDCl3) δ 7.72 (d, J=8.4 Hz, 1H), 7.48 (d, J=8.4 Hz, 1H), 7.40~7.50 (m, 1H), 7.27 (s, 1H), 7.26 (d, J=8.8 Hz, 2H), 7.02 (d, J=2.0 Hz, 1H), 5.81 (s, 1H), 4.70~4.90 (m, 1H), 1.43 (s, 9H).

tert-butyl [2-(4-bromobenzoyl)-4-chlorophenyl]carbamate (7-3)

To a solution of tert-butyl {2-[(4-bromophenyl)(hydroxy)methyl]-4-chlorophenyl}carbamate (10 g, 25 mmol) in 100 ml CH$_2$Cl$_2$, was added MnO$_2$ (10 g, 125 mmol) and the mixture was heated to 35° C. for 48 hours. Filtration and concentration gave tert-butyl [2-(4-bromobenzoyl)-4-chlorophenyl]carbamate as a yellow solid. $^1$HNMR: (400 MHz, CDCl3) δ 9.77 (s, 1H), 8.39 (d, J=8.8 Hz, 1H), 7.65 (d, J=8.4 Hz, 2H), 7.57 (d, J=8.4 Hz, 2H), 7.49 (dd, J=8.8, 2.0 Hz, 1H), 7.42 (d, J=2.4 Hz, 1H), 1.51 (s, 9H).

N-[4-chloro-2-(4-bromobenzoyl)phenyl]-1H-imidazole-1-carboxamide (7-4)

To a solution of tert-butyl [2-(4-bromobenzoyl)-4-chlorophenyl]carbamate (10 g, 25 mmol) in MeOH (50 mL) at 25° C. was added 2 M HCl-MeOH (100 ml), and the reaction mixture stirred for 4 h. The organic layer was evaporated, then the residue was partitioned between CH$_2$Cl$_2$ (300 ml) and water (200 ml). The organic layer was washed with 10% Na$_2$CO$_3$ (to pH=9) and brine, dried over Na$_2$SO$_4$ and evaporated to give 7.5 g (98% yield) (2-amino-5-chlorophenyl)(4-bromophenyl)methanone. To a solution of (2-amino-5-chlorophenyl)(4-bromophenyl)methanone (13 g, 42 mmol) in 500 ml CH$_2$Cl$_2$ was added solid carbonyldiimidazole (15.7 g, 96 mmol) portionwise. The resulting yellow solution was allowed to stir at 40° C. for 16 hrs, concentrated to give a yellow foam. The foam was treated with 30 ml of ether and 20 ml of water with vigorous stirring resulting in a solid precipitate. After filtration, the cake was recrystallized from CH$_2$Cl$_2$/Ether (1:5) to give N-[4-chloro-2-(4-bromobenzoyl)phenyl]-1H-imidazole-1-carboxamide as a yellow solid. $^1$HNMR: (400 MHz, DMSO-d$_6$) δ 11.05 (s, 1H), 7.69 (d, J=8.4 Hz, 2H), 7.55 (dd, J=8.4, 1.6 Hz, 1H), 7.33 (s, 1H), 6.98~7.10 (m, 5H), 6.71 (d, J=2.0 Hz, 1H).

6-chloro-4-(4-bromophenyl)-4-hydroxy-3-(2,2,2-trifluoroethyl)-3,4-dihydroquinazolin-2(1H)-one (7-5)

To a solution of N-[4-chloro-2-(4-bromobenzoyl)phenyl]-1H-imidazole-1-carboxamide (4.0 g, 9.9 mmol) in THF (20 mL) was added 2,2,2-trifluoroethylamine (1.1 g, 10.9 mmol). The reaction was heated to 50° C. After 19 h at 50° C., the reaction was cooled to ambient temperature and concentrated in vacuo. The light yellow foam was partitioned between n-butyl chloride (15 mL) and aqueous 10% citric acid (15 mL) with vigorous stirring. The resulting precipitate was collected by vacuum filtration to give 6-chloro-4-(4-bromophenyl)-4-hydroxy-3-(2,2,2-trifluoroethyl)-3,4-dihydroquinazolin-2(1H)-one as a white solid. 1H NMR (CDCl$_3$, 500 MHz) δ 7.98 (s, 1H); 7.50 (br d, 2H, J=8.79 Hz); 7.34 (br d, 2H, J=8.79 Hz); 7.22 (m, 2H); 6.97 (dd, J=1.46 and 7.57 Hz, 1H); 4.35 (dq, 1H, J=8.78 and 16 Hz); 3.53 (dq, 1H, J=8.55 and 17 Hz); 3.22 (s, 1H). MS (Electrospray): m/z M+Na, Br=79, 457.0

6-Chloro-4-ethyl-4-(4-bromophenyl)-3-(2,2,2-trifluoroethyl)-3,4-dihydroquinazolin-2(1H)-one To a −18° C. solution of 6-chloro-4-(4-bromophenyl)-4-hydroxy-3-(2,2,2-trifluoroethyl)-3,4-dihydroquinazolin-2(1H)-one (1 g, 2.3 mmol) in anhydrous THF (10 mL) was added triethylamine (1.6 mL, 11 mmol). The reaction was stirred for 5 min and then thionyl chloride (0.18 mL, 2.5 mmol) was added dropwise. After 10 min, 1M ethylmagnesium bromide in THF (9 mL, 9 mmol) was added. The reaction mixture was warmed from −18° C. to 0° C. and allowed to stir for 30 min and then quenched with 15 mL 1N aqueous HCl and extracted with 50 mL ethyl acetate. The organic layer was washed with brine (60 mL), dried over MgSO$_4$, filtered, and concentrated in vacuo. Purification by normal phase chromatography (90 g silica gel cartridge, linear gradient 10-70% EtOAc/hexanes) gave 6-chloro-4-ethyl-4-(4-bromophenyl)-3-(2,2,2-trifluoroethyl)-3,4-dihydroquinazolin-2(1H)-one as an off-white solid. 1H NMR (CDCl$_3$, 500 MHz) δ 8.41 (s, NH); 7.53 (br d, 2H, J=8.79 Hz); 7.28 (br d, 2H, J=8.54 Hz); 7.11 (dd, 1H, J=8.54 and 2.19 Hz); 6.69 (d, 1H, J=8.55 Hz); 6.46 (d, 1H, J=2.20 Hz); 3.87 (dq, 1H, J=9.28 and 16 Hz); 3.52 (dq, 1H, J=8.30 and 17 Hz); 2.39 (dq, 1H, J=7.08 and 14 Hz); 2.22 (dq, 1H, J=7.08 and 14 Hz); 0.90 (t, J=7.08 Hz, 3H); MS (Electrospray): m/z 447.1 (M$^+$H, Br=79).

EXAMPLE 11

6-Chloro-4-ethyl-4-(4-cyanophenyl)-3-(2,2,2-trifluoroethyl)-3,4-dihydroquinazolin-2(1H)-one (7-6)

To a solution of 0.062 g (0.14 mmol) 6-chloro-4-ethyl-4-(4-bromophenyl)-3-(2,2,2-trifluoroethyl)-3,4-dihydroquinazolin-2(1H)-one in 1 mL DMF was added 0.015 g (0.17 mmol) copper(I) cyanide and the mixture heated in a sealed tube at 200° C. for 2 hours. After cooling to room temperature, the mixture was filtered and the resulting DMF solution purified by preperative reverse phase chromatography (linear gradient 5 to 95% CH$_3$CN/H$_2$O over 30 min, 0.05% added TFA, C18 SunFire 19×150 mm) to provide 6-chloro-4-ethyl-4-(4-cyanophenyl)-3-(2,2,2-trifluoroethyl)-3,4-dihydroquinazolin-2(1H)-one. 1H NMR (CDCl$_3$, 400 MHz) δ 8.06 (s, NH); 7.71 (br d, 2H, J=8.24 Hz); 7.55 (br d, 2H, J=8.43 Hz); 7.14 (dd, 1H, J=8.61 and 2.20 Hz); 6.69 (d, 2H, J=8.61 Hz); 6.43 (d, 1H, J=2.02 Hz); 3.78 (dq, 1H, J=8.97 and 18 Hz); 3.60 (dq, 1H, J=8.43 and 17 Hz); 2.44 (dq, 1H, J=7.15 and 14 Hz); 2.27 (dq, 1H, J=7.14 and 14 Hz); 0.93 (t, J=7.15 Hz, 3H); MS (Electrospray): exact mass calculated for C$_{19}$H$_{15}$ClF$_3$N$_3$O+H 394.0929 found 394.0937

EXAMPLE 12

6-Chloro-4-cyclopropyl-4-(4-bromophenyl)-3-(2,2,2-trifluoroethyl)-3,4-dihydroquinazolin-2(1H)-one To a −18° C. solution of 6-chloro-4-(4-bromophenyl)-4-hydroxy-3-(2,2,2-trifluoroethyl)-3,4-dihydroquinazolin-2(1H)-one (2 g, 4.6 mmol) in anhydrous THF (20 mL) was added triethylamine (2.6 mL, 18 mmol). The reaction was stirred for 5 min and then thionyl chloride (0.0.37 mL, 5 mmol) was added dropwise. After 10 min, 0.5M cyclopropylmagnesium bromide in THF (36 mL, 18 mmol) was added. The reaction mixture was warmed from −18° C. to 0° C. and allowed to stir for 6 hours and then quenched with 25 mL 1N aqueous HCl and extracted with 150 mL ethyl acetate. The organic layer was washed with brine (100 mL), dried over MgSO$_4$, filtered, and concentrated in vacuo. Purification by normal phase chromatography (120 g silica gel cartridge, linear gradient 10-70% EtOAc/hexanes) followed by crystallization from hexanes gave 6-chloro-4-cyclopropyl-4-(4-bromophenyl)-3-(2,2,2-trifluoroethyl)-3,4-dihydroquinazolin-2(1H)-one as a green solid. 1H NMR (CDCl$_3$, 400 MHz) δ 7.56 (s, NH); 7.46 (br d, 2H, J=8.61 Hz); 7.21 (dd, 1H, J=8.42 and 2.20 Hz); 7.12 (br d, 2H, J=7.14 Hz); 6.85 (br m, 1H); 6.68 (d, 1H, J=8.24 Hz); 4.27 (m, 2H); 1.6 (obs, 1H); 0.77 (m, 2H); 0.19 (m, 1H); 0.09 (m, 1H); MS (Electrospray): m/z 459.0 (M$^+$H, Br=79).

EXAMPLE 13

6-Chloro-4-cyclopropyl-4-(4-cyanophenyl)-3-(2,2,2-trifluoroethyl)-3,4-dihydroquinazolin-2(1H)-one To a solution of 0.39 g (0.85 mmol) 6-chloro-4-cyclopropyl-4-(4-bromophenyl)-3-(2,2,2-trifluoroethyl)-3,4-dihydroquinazolin-2(1H)-one in 2.5 mL DMF was added 0.13 g (1.4 mmol) copper(I) cyanide and the mixture heated in a sealed tube at 190° C. for 2 hours. After cooling to room temperature, the reaction mixture was diluted with 125 mL ether, washed 2×100 mL water and 1×100 mL brine, dried over dried over MgSO$_4$, filtered, and concentrated in vacuo. Purification by normal phase chromatography (40 g silica gel cartridge, linear gradient 5-75% EtOAc/hexanes) followed by preperative chiral chromatography (5×50 mm Chiralcel OD, 100% MeOH) provided the first peak (−) 6-chloro-4-cyclopropyl-4-(4-cyanophenyl)-3-(2,2,2-trifluoroethyl)-3,4-dihydroquinazolin-2(1H)-one. Optical rotation −83° (c=0.00175 g/mL in CH$_2$Cl$_2$, Na lamp,) 1H NMR (CDCl$_3$, 400 MHz) δ 8.18 (s, NH); 7.64 (br d, 2H, J=7.88 Hz); 7.39 (br d, 2H, J=6.22 Hz); 7.26 (obscured, 1H); 6.85 (br m, 1H); 6.74 (d, 1H, J=8.24 Hz); 4.34 (m, 1H); 4.23 (br m, 1H); 1.62 (m, 1H); 0.82 (m, 2H); 0.20 (m, 1H); 0.097 (m, 1H); MS (Electrospray): exact mass calculated for C$_{20}$H$_{15}$ClF$_3$N$_3$O+H 406.0925 found 406.0935 Collect 0.1 g second peak Optical rotation +100° (c=0.002 g/mL in CH$_2$Cl$_2$, Na lamp,).

EXAMPLE 14

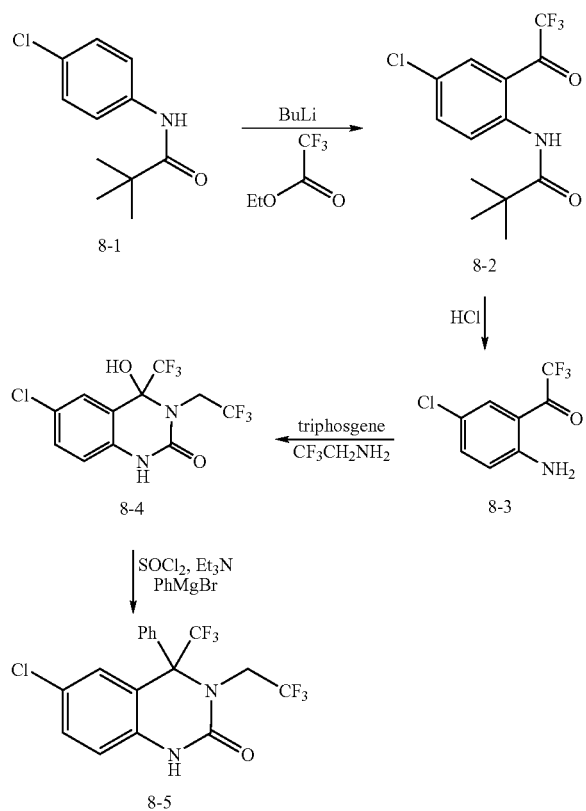

N-[4-Chloro-2-(trifluoroacetyl)phenyl]-2,2-dimethyl-propanamide (8-2)

To a −40° C. mixture of N-(4-chlorophenyl)-2,2-dimethylpropanamide (4.0 g, 18.9 mmol) and anhydrous tetrahydrofuran (38 ml), n-butyllithium (1.6M, 45.2 mmol) was added under nitrogen atmosphere. The reaction was stirred for 30 minutes at −40° C. and allowed to warm to 0° C. where upon the yellow homogenous mixture turned gradually darker to a deep yellow color. After 30 minutes of stirring at 0° C., the reaction was cooled to 40° C. Ethyl trifluoroacetate (6.1 g, 43.5 mmol) was added to the mixture and allowed to warm to room temperature overnight. The reaction was quenched with water (100 ml) and saturated aqueous ammonium chloride solution (80 ml). The aqueous layer was extracted with ethyl acetate (3×75 ml). Combined organic extracts were dried over MgSO$_4$, filtered and concentrated in vacuo to afford a dark yellow oil. Flash chromatography on silica gel (0-50% ethyl acetate/hexanes) afforded N-[4-chloro-2-(trifluoroacetyl)phenyl]-2,2-dimethyl-propanamide. $^1$H NMR (CDCl$_3$, 400 MHz) δ 11.15 (s), 8.89 (d, J=9.2 Hz, 1H), 7.92 (m, 1H), 7.65 (dd, J=2.4 and 9.2 Hz, 1H), 1.36 (s, 9H). MS (Electrospray): m/z 308.0 (M+).

1-(2-Amino-5-chlorophenyl)-2,2,2-trifluoroethanone (8-3)

6N Hydrochloric acid (6.0M, 257 mmol) was added to N-[4-chloro-2-(trifluoroacetyl)phenyl]-2,2-dimethylpropanamide (3.3 g, 10.7 mmol) in anhydrous dimethoxyethane (40 ml) at room temperature and mixture was heated to reflux conditions for two hours until no starting material was observed by LC/MS. After cooling reaction to 0° C., reaction was basified to pH 9 by adding solid sodium bicarbonate in portions. Reaction was extracted with ethyl acetate (3×150 ml), and combined organic extracts were dried over MgSO$_4$ and Na$_2$SO$_4$. After filtering mixture, the collected filtrate was concentrated in vacuo to give a crude yellow solid. Flash chromatography of the crude solid on silica gel (0-25% ethyl acetate/hexanes) afforded 1-(2-amino-5-chlorophenyl)-2,2,2-trifluoroethanone as a yellow solid. $^1$H NMR (CDCl$_3$, 400 MHz) δ 7.70 (m, 1H), 7.32 (dd, J=2.4 and 9.2 Hz, 1H), 6.68 (d, J=8.8 Hz, 1H), 6.46 (s, 2H). MS (Electrospray): m/z 223.9 (M+).

6-Chloro-4-hydroxy-3-(2,2,2-trifluoroethyl)-4-(trifluoromethyl)-3,4-dihydro-quinazolin-2(1H)-one (8-4)

A mixture of triethylamine (1.3 ml, 9.4 mmol) and 1-(2-amino-5-chlorophenyl)-2,2,2-trifluoroethanone (2.1 g, 9.4 mmol) in diethyl ether (18 ml) was cooled to 0° C. under nitrogen atmosphere. In a separate round bottom, triphosgene (929 mg, 3.1 mmol) in diethyl ether (11 ml) was cooled to 0° C. To the phosgene mixture at 0° C. was added dropwise the trifluoroethanone mixture. After stirring for 15 minutes, to this reaction was added a mixture of triethylamine (1.3 ml, 9.4 mmol) and trifluoroethylamine in diethyl ether (18 ml). The reaction stirred for two hours at room temperature and then quenched with water (50 ml) and washed with saturated aqueous sodium bicarbonate solution (2×30 ml). The aqueous layer was extracted with ethyl acetate (3×100 ml) and the combined organic extracts were dried over Na$_2$SO$_4$, filtered and concentrated to give crude material which was purified by flash chromatography on silica gel (0-30% ethyl acetate/hexanes). This afforded 6-chloro-4-hydroxy-3-(2,2,2-trifluoroethyl)-4-(trifluoromethyl)-3,4-dihydroquinazolin-2(1H)-one as a yellow solid. $^1$H NMR (CDCl$_3$, 400 MHz) δ 9.22 (s, 1H), 7.58 (s, 1H), 7.39 (dd, J=2.0 and 8.6 Hz, 1H), 6.84 (d, J=8.4 Hz, 1H), 4.71 (m, 1H), 4.38 (s, 1H), 4.18 (m, 1H). Exact Mass (Electrospray, M+H): Calc'd, 349.0173; Found, 349.0166.

6-Chloro-4-phenyl-3-(2,2,2-trifluoroethyl)-4-(trifluoromethyl)-3,4-dihydro-quinazolin-2 (1H)-one (8-5)

To a −78° C. mixture of 6-chloro-4-hydroxy-3-(2,2,2-trifluoroethyl)-4-(trifluoromethyl)-3,4-dihydroquinazolin-2 (1H)-one (214 mg, 0.6 mmol) and tetrahydrofuran (2.0 ml) was added triethylamine (0.4 ml, 3.1 mmol) under nitrogen atmosphere. After stirring mixture at −78° C. for 20 minutes, thionyl chloride (0.05 ml, 0.64 mmol) was added dropwise whereupon a yellow solid precipitated in the reaction mixture forming a thick yellow emulsion. After the emulsion was stirred at −78° C. for 30 minutes, 3.0M phenyl magnesium bromide was added. Reaction was allowed to stir for one hour until no further increase in desired product was observed by LC/MS. Reaction was quenched with saturated aqueous ammonium chloride solution (10 ml) at −78° C. and mixture was allowed to warm to room temperature. Mixture was extracted with ethyl acetate (3×20 ml) and combined organic extracts were dried over Na$_2$SO$_4$, filtered and concentrated in vacuo. The resulting crude oil was purified by flash chromatography on silica gel (0-30% ethyl acetate/hexanes) to afford an oil which was further purified by reverse phase prep HPLC to give 6-chloro-4-phenyl-3-(2,2,2-trifluoroethyl)-4-(trifluoromethyl)-3,4-dihydroquinazolin-2(1H)-one as colorless oil. $^1$H NMR (CD$_3$OD, 400 MHz) δ 7.52 (m, 5H), 7.34 (dd, J=2.4 and 8.4 Hz, 1H), 6.95 (d, J=8.4 Hz, 1H), 6.4 (m, 1H), 4.29 (m, 1H), 3.62 (m, 1H). Exact Mass (Electrospray, M+H): Calc'd, 409.0537; Found, 409.0533.

EXAMPLE 15

6-Chloro-4-(fluorophenyl)-3-(2,2,2-trifluoroethyl)-4-(trifluoromethyl)-3,4-dihydroquinazolin-2(1H)-one Utilizing the general procedure outlined for 6-chloro-4-phenyl-3-(2,2,2-trifluoroethyl)-4-(trifluoromethyl)-3,4-dihydroquinazolin-2(1H)-one, 6-chloro-4-hydroxy-3-(2,2,2-trifluoroethyl)-4-(trifluoromethyl)-3,4-dihydroquinazolin-2(1H)-one (100 mg, 0.29 mmol) was reacted with 1.0 M 4-fluorophenyl magnesium bromide (1.0 ml, 1.0 mmol) to afford 6-chloro-4-(fluorophenyl)-3-(2,2,2-trifluoroethyl)-4-(trifluoromethyl)-3,4-dihydro-uinazolin-2(1H)-one as a white solid. $^1$H NMR (CD$_3$OD, 400 MHz) δ 9.50 (s, 1H), 7.51 (m, 2H), 7.29 (dd, J=2.4 and 8.6 Hz, 1H), 7.17 (m, 2H), 6.83 (d, J=8.4 Hz, 1H), 6.53 (s, 1H), 4.43 (m, 1H), 3.52 (m, 1H). Exact Mass (Electrospray, M+H): Calc'd, 427.0443; Found, 427.0430.

EXAMPLE 16

6-Chloro-4-ethyl-3-(2,2,2-trifluoroethyl)-4-(trifluoromethyl)-3,4-dihydro-quinazolin2(1H)-one Utilizing the general procedure outlined for 6-chloro-4-phenyl-3-(2,2,2-trifluoroethyl)-4-(trifluoromethyl)-3,4-dihydroquinazolin-2(1H)-one, 6-chloro-4-hydroxy-3-(2,2,2-trifluoroethyl)-4-(trifluoromethyl)-3,4-dihydroquinazolin-2(1H)-one (227 mg, 0.65 mmol) was reacted with 3.0M ethyl magnesium bromide (0.9 ml, 2.6 mmol) to afford 6-chloro-4-ethyl-3-(2,2,2-trifluoroethyl)-4-(trifluoromethyl)-3,4-dihydroquinazolin2(1H)-one as a white solid. $^1$H NMR (d$_6$-DMSO, 400 MHz) δ 7.41 (s, 1H), 7.35 (dd, J=2.4 and 8.6 Hz, 1H), 6.88 (d, J=8.8 Hz, 1H), 4.52 (m, 1H), 4.26 (m, 1H), 2.55 (m, 1H), 2.36 (m, 1H), 0.9 (t, J=6.8 Hz, 3H). Exact Mass (Electrospray, M+H) Calc'd, 361.0537; Found, 361.0532.

EXAMPLE 17

6-Chloro-4-allyl-3-(2,2,2-trifluoroethyl)-4-trifluoromethyl)-3,4-dihydro-quinazolin-2(1H)-one Utilizing the general procedure outlined for 6-chloro-4-phenyl-3-(2,2,2-trifluoroethyl)-4-(trifluoromethyl)-3,4-dihydroquinazolin-2(1H)-one, 6-chloro-4-hydroxy-3-(2,2,2-trifluoroethyl)-4-(trifluoromethyl)-3,4-dihydroquinazolin-2(1H)-one (374 mg, 1.1 mmol) was reacted with 1.0M allyl magnesium bromide (6.4 ml, 6.4 mmol) to afford 4-allyl-6-chloro-3-(2,2,2-trifluoroethyl)-4-(trifluoromethyl)-3,4-dihydroquinazolin-2(1H)-one as a colorless oil. $^1$H NMR (CDCl$_3$, 400 MHz) δ 9.88 (s, 1H), 7.29 (dd, J=2.4 and 8.6 Hz, 1H), 7.17 (s, 1H), 6.80 (d, J=8.8 Hz, 1H), 5.53 (m, 1H), 5.22 (m, 2H), 4.56 (m, 1H), 4.12 (m, 1H), 3.11 (m, 2H). MS (Electrospray): m/z 373.0 (M+).

EXAMPLE 18

6-Chloro-4-propyl-3-(2,2,2-trifluoroethyl)-4-(trifluoromethyl)-3,4-dihydro-quinazolin-2(1H)-one A mixture of 4-allyl-6-chloro-3-(2,2,2-trifluoroethyl)-4-(trifluoromethyl)-3,4-dihydroquinazolin-2(1H)-one (42 mg, 0.11 mmol), ethyl acetate (3.5 ml) and 10% Pd/C (10 mg) was placed under hydrogen atmosphere (1 atm) at room temperature and stirred overnight. After bubbling nitrogen through reaction mixture, the mixture was filtered through a Celite, washing with ethyl acetate. The collected filtrate was concentrated to give an oil which was purified by reverse phase prep HPLC to afford 6-chloro-4-propyl-3-(2,2,2-trifluoroethyl)-4-(trifluoromethyl)-3,4-dihydroquinazolin-2(1H)-one as a white solid. $^1$H NMR (CD$_3$OD, 400 MHz) δ 7.40 (s, 1H), 7.35 (dd, J=2.4 and 8.6 Hz, 1H), 6.86 (d, J=8.8 Hz 1H), 4.45 (m, 1H), 4.27 (m, 1H), 2.47 (m, 1H), 2.17 (m, 1H), 1.23 (m, 2H), 0.96 (t, J=7.2 Hz, 3H).

Exact Mass (APCI, M+) Calc'd, 375.0644; Found, 375.0686.

EXAMPLE 19

4-Butyl-6-chloro-3-(2,2,2-trifluoroethyl)-4-(trifluoromethyl)-3,4-dihydroquinazolin-2(1H)-one Utilizing the general procedure outlined for 6-chloro-4-phenyl-3-(2,2,2-trifluoroethyl)-4-(trifluoromethyl)-3,4-dihydroquinazolin-2(1H)-one, 6-chloro-4-hydroxy-3-(2,2,2-trifluoroethyl)-4-(trifluoromethyl)-3,4-dihydroquinazolin-2(1H)-one (100 mg, 0.3 mmol) was reacted with 1.0M butyl magnesium chloride (1.0 ml, 1.0 mmol) to afford 4-butyl-6-chloro-3-(2,2,2-trifluoroethyl)-4-(trifluoromethyl)-3,4-dihydroquinazolin-2(1H)-one as an oil. $^1$H NMR (CD$_3$OD, 400 MHz) δ 7.41 (s, 1H), 7.35 (dd, J=2.4 and 8.4 Hz, 1H), 6.9 (d, J=8.4 Hz, 1H), 4.55 (m, 1H), 4.29 (m, 1H), 2.50 (m, 1H), 2.22 (m, 1H), 1.40 (m, 2H), 1.24 (m, 1H), 1.13 (m, 1H), 0.90 (m, 3H). Exact Mass (Electrospray, M+H) Cal'd, 389.0850; Found, 389.0850.

EXAMPLE 20

6-Chloro-4-cyclopropyl-3-(2,2,2-trifluoroethyl)-4-(trifluoromethyl)-3,4-dihydro-quinazolin-2(1H)-one Utilizing the general procedure outlined for 6-chloro-4-phenyl-3-(2,2,2-trifluoroethyl)-4-(trifluoromethyl)-3,4-dihydroquinazolin-2(1H)-one, 6-chloro-4-hydroxy-3-(2,2,2-trifluoroethyl)-4-(trifluoromethyl)-3,4-dihydroquinazolin-2(1H)-one (217 mg, 0.62 mmol) was reacted with 0.5 M cyclopropyl magnesium bromide (4.9 ml, 2.5 mmol) to afford 6-chloro-4-cyclopropyl-3-(2,2,2-trifluoroethyl)-4-(trifluoromethyl)-3,4-dihydroquinazolin-2(1H)-one as an oil. $^1$H NMR (CD$_3$OD, 400 MHz) δ 7.89 (d, J=2.0 Hz, 1H), 7.36 (dd, J=2.4 and 8.6 Hz), 1H), 6.91 (dd, J=1.6 Hz and 7.6 Hz, 1H), 4.74 (m, 1H), 4.52 (m, 1H), 1.50 (m, 1H), 1.26 (m, 2H), 1.15 (m, 1H), 1.02 (m, 1H). Exact Mass (Electrospray, M+H) Calc'd, 373.0537; Found, 373.0541.

EXAMPLE 21

6-Chloro-4-(cyclopropylethyl)-3-(2,2,2-trifluoroethyl)-4-(trifluoromethyl)-3,4-dihydroquinazolin-2((1H)-one 3.0 M Ethyl magnesium bromide (0.29 ml, 0.86 mmol) was added dropwise to a mixture of cyclopropylacetylene (0.1 ml, 1.1 mmol) in anhydrous tetrahydrofuran (1.5 ml) at room temperature under nitrogen atmosphere. Vigorous bubbling was observed as mixture was allowed to stir for 40 minutes. In a separate round bottom, thionyl chloride (0.022 ml, 0.3 mmol) was added to a −78° C. mixture of 6-chloro-4-hydroxy-3-(2,2,2-trifluoroethyl)-4-(difluoromethyl)-3,4-dihydroquinazolin-2(1H)-one (100 mg, 0.29 mmol), triethylamine (0.2 ml, 1.4 mmol) and tetrahydrofuran (2.0 ml). After reaction was allowed to stir at −78° C. for 30 minutes, the cyclopropylacetylene mixture was added. By LC/MS, less than ten percent of desired product was observed in the reaction. An additional 3.0 equivalents of cyclopropyl acetylene Grignard reagent was added to reaction and stirred for 40 minutes at −78° C. Reaction was quenched with saturated aqueous ammonium chloride solution. The aqueous layer was extracted with ethyl acetate (3×20 ml) and combined organic extracts were dried over $Na_2SO_4$, filtered and concentrated in vacuo to give a crude oil which was purified by flash chromatography on silica gel (0-35% ethyl acetate/hexanes). This gave an oil which was further purified by reverse phase prep HPLC to afford 6-chloro-4-(cyclopropylethynyl)-3-(2,2,2-trifluoroethyl)-4-(trifluoromethyl)-3,4-dihydroquinazolin-2((1H)-one as a white solid. $^1$H NMR (CD$_3$OD, 400 MHz) δ 7.55 (s, 1H), 7.41 (m, 1H), 6.92 (d, J=8.4 Hz, 1H), 4.71 (m, 1H), 4.25 (m, 1H), 1.54 (m, 1H), 0.98 (m, 2H), 0.82 (m, 2H). Exact Mass (Electrospray, M+H) Calc'd, 397.0537; Found, 397.0515.

TABLE 1

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH$^+$) m/z |
|---|---|---|
| 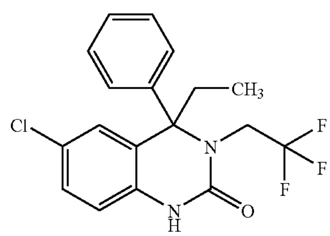 | 6-CHLORO-4-ETHYL-4-PHENYL-3-(2,2,2-TRIFLUOROETHYL)-3,4-DIHYDROQUINAZOLIN-2(1H)-ONE | 369.0 |
| 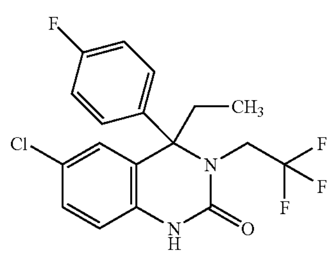 | 6-CHLORO-4-ETHYL-4-(4-FLUOROPHENYL)-3-(2,2,2-TRIFLUOROETHYL)-3,4-DIHYDROQUINAZOLIN-2(1H)-ONE | 387.0 |
| 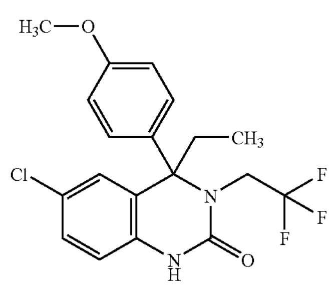 | 6-CHLORO-4-ETHYL-4-(-4-METHOXYPHENYL)-3-(2,2,2-TRIFLUOROETHYL)-3,4-DIHYDROQUINAZOLIN-2(1H)-ONE | 399.0 |
| 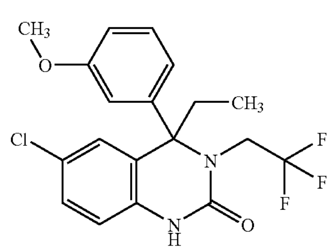 | 6-CHLORO-4-ETHYL-4-(-3-METHOXYPHENYL)-3-(2,2,2-TRIFLUOROETHYL)-3,4-DIHYDROQUINAZOLIN-2(1H)-ONE | 399.0 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH+) m/z |
|---|---|---|
| 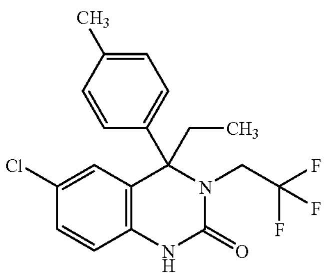 | 6-CHLORO-4-ETHYL-4-(4-METHYLPHENYL)-3-(2,2,2-TRIFLUOROETHYL)-3,4-DIHYDROQUINAZOLIN-2(1H)-ONE | 383.0 |
| 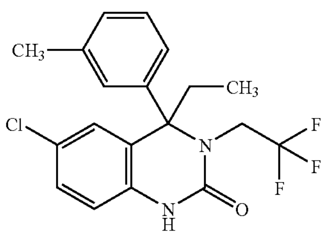 | 6-CHLORO-4-ETHYL-4-(3-METHYLPHENYL)-3-(2,2,2-TRIFLUOROETHYL)-3,4-DIHYDROQUINAZOLIN-2(1H)-ONE | 383.0 |
| 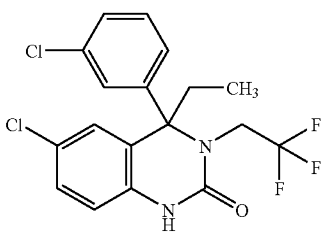 | 6-CHLORO-4-ETHYL-4-(3-CHLOROPHENYL)-3-(2,2,2-TRIFLUOROETHYL)-3,4-DIHYDROQUINAZOLIN-2(1H)-ONE | 403.0 |
| 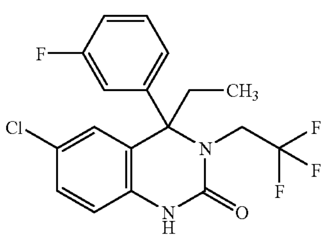 | 6-CHLORO-4-ETHYL-4-(3-FLUOROPHENYL)-3-(2,2,2-TRIFLUOROETHYL)-3,4-DIHYDROQUINAZOLIN-2(1H)-ONE | 387.0 |
| 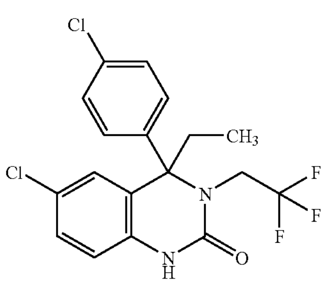 | 6-CHLORO-4-ETHYL-4-(4-CHLOROPHENYL)-3-(2,2,2-TRIFLUOROETHYL)-3,4-DIHYDROQUINAZOLIN-2(1H)-ONE | 403.0 |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| STRUCTURE | NAME | parent ion (MH$^+$) m/z |
|---|---|---|
| 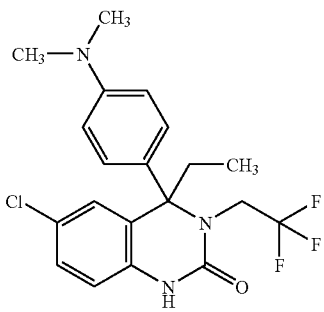 | 6-CHLORO-4-ETHYL-4-(4-DIMETHYLAMINOPHENYL)-3-(2,2,2-TRIFLUOROETHYL)-3,4-DIHYDROQUINAZOLIN-2(1H)-ONE | 412.1 |
| 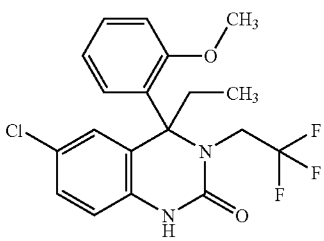 | 6-CHLORO-4-ETHYL-4-(2-METHOXYPHENYL)-3-(2,2,2-TRIFLUOROETHYL)-3,4-DIHYDROQUINAZOLIN-2(1H)-ONE | 399.1 |
| 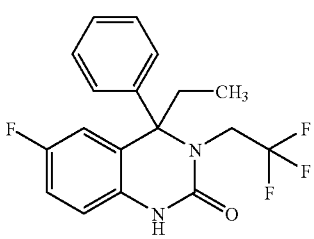 | 6-FLUORO-4-ETHYL-4-PHENYL-3-(2,2,2-TRIFLUOROETHYL)-3,4-DIHYDROQUINAZOLIN-2(1H)-ONE | 353.1 |
| 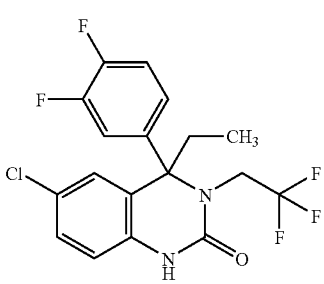 | 6-CHLORO-4-ETHYL-4-(3,4-DIFLUOROPHENYL)-3-(2,2,2-TRIFLUOROETHYL)-3,4-DIHYDROQUINAZOLIN-2(1H)-ONE | 405.1 |
| 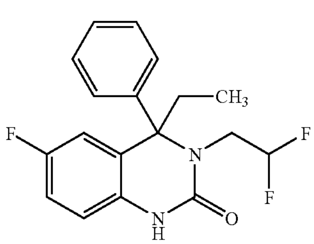 | 6-FLUORO-4-ETHYL-4-PHENYL-3-(2,2-DIFLUOROETHYL)-3,4-DIHYDROQUINAZOLIN-2(1H)-ONE | 335.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH+) m/z |
|---|---|---|
| 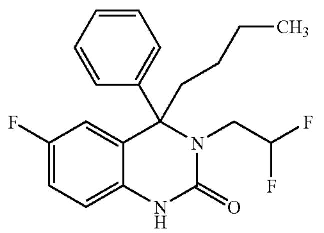 | 6-FLUORO-4-BUTYL-4-PHENYL-3-(2,2-DIFLUOROETHYL)-3,4-DIHYDROQUINAZOLIN-2(1H)-ONE | 363.2 |
| 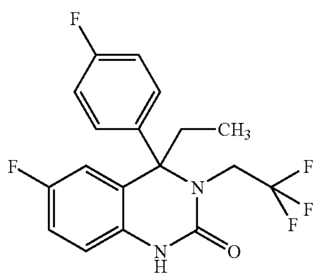 | 6-FLUORO-4-ETHYL-4-(4-FLUOROPHENYL)-3-(2,2,2-TRIFLUOROETHYL)-3,4-DIHYDROQUINAZOLIN-2(1H)-ONE | 371.1 |
| 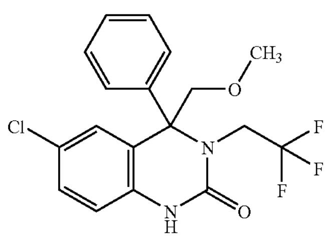 | 6-CHLORO-4-METHOXYMETHYL-4-PHENYL-3-(2,2,2-TRIFLUOROETHYL)-3,4-DIHYDROQUINAZOLIN-2(1H)-ONE | 385.1 |
| 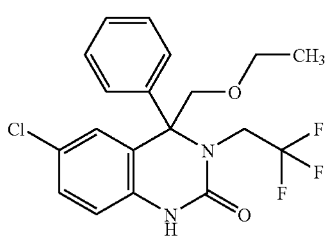 | 6-CHLORO-4-ETHOXYMETHYL-4-PHENYL-3-(2,2,2-TRIFLUOROETHYL)-3,4-DIHYDROQUINAZOLIN-2(1H)-ONE | 399.1 |
| 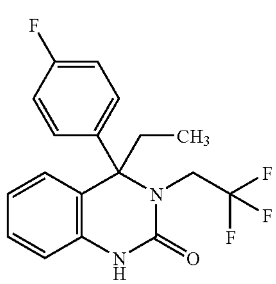 | 4-ETHYL-4-(4-FLUORO-PHENYL)-3-(2,2,2-TRIFLUOROETHYL)-3,4-DIHYDROQUINAZOLIN-2(1H)-ONE | 353.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH$^+$) m/z |
|---|---|---|
| 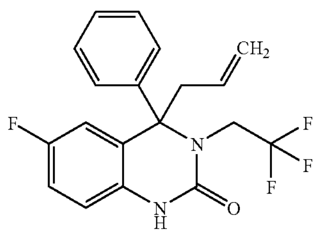 | 6-FLUORO-4-ALLYL-4-PHENYL-3-(2,2,2-TRIFLUOROETHYL)-3,4-DIHYDROQUINAZOLIN-2(1H)-ONE | 365.1 |
| 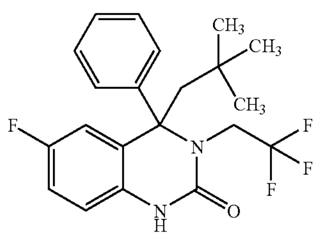 | 6-FLUORO-4-(2,2-DIMETHYLPROPYL)-4-PHENYL-3-(2,2,2-TRIFLUOROETHYL)-3,4-DIHYDROQUINAZOLIN-2(1H)-ONE | 395.2 |
| 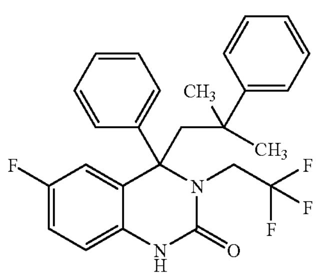 | 6-FLUORO-4-(2-PHENYL-2-METHYLPROPYL)-4-PHENYL-3-(2,2,2-TRIFLUOROETHYL)-3,4-DIHYDROQUINAZOLIN-2(1H)-ONE | 457.2 |
| 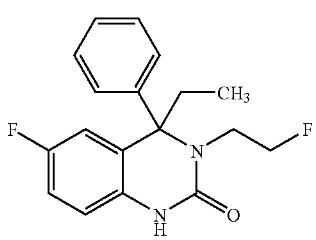 | 6-FLUORO-4-ETHYL-4-PHENYL-3-(2-FLUOROETHYL)-3,4-DIHYDROQUINAZOLIN-2(1H)-ONE | 317.1 |
| 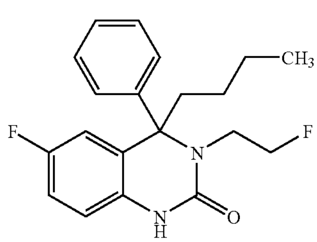 | 6-FLUORO-4-BUTYL-4-PHENYL-3-(2-FLUOROETHYL)-3,4-DIHYDROQUINAZOLIN-2(1H)-ONE | 345.2 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH$^+$) m/z |
|---|---|---|
| 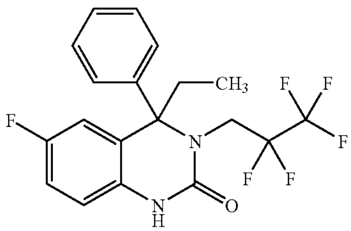 | 6-FLUORO-4-ETHYL-4-PHENYL-3-(2,2,3,3,3-PENTAFLUOROPROPYL)-3,4-DIHYDROQUINAZOLIN-2(1H)-ONE | 403.1 |
| 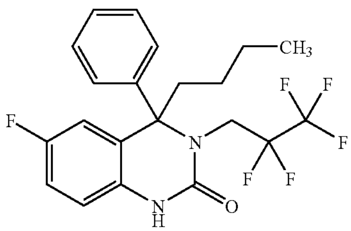 | 6-FLUORO-4-BUTYL-4-PHENYL-3-(2,2,3,3,3-PENTAFLUOROPROPYL)-3,4-DIHYDROQUINAZOLIN-2(1H)-ONE | 431.2 |
| 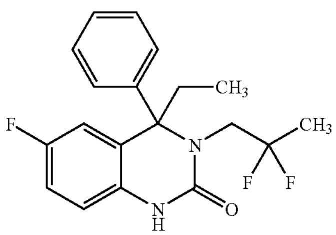 | 6-FLUORO-4-ETHYL-4-PHENYL-3-(2,2-DIFLUOROPROPYL)-3,4-DIHYDROQUINAZOLIN-2(1H)-ONE | 349.2 |
| 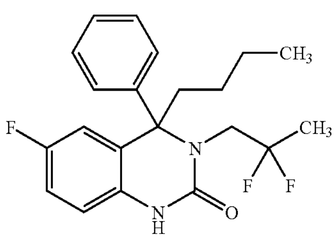 | 6-FLUORO-4-BUTYL-4-PHENYL-3-(2,2-DIFLUOROPROPYL)-3,4-DIHYDROQUINAZOLIN-2(1H)-ONE | 377.2 |
| 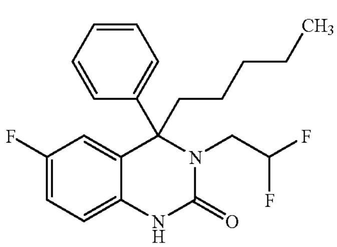 | 6-FLUORO-4-PENTYL-4-PHENYL-3-(2,2-DIFLUOROETHYL)-3,4-DIHYDROQUINAZOLIN-2(1H)-ONE | 377.2 |
| 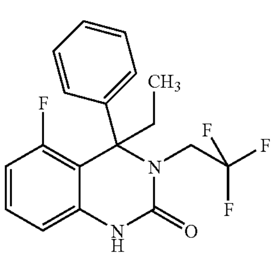 | 5-FLUORO-4-ETHYL-4-PHENYL-3-(2,2,2-TRIFLUOROETHYL)-3,4-DIHYDROQUINAZOLIN-2(1H)-ONE | 353.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH+) m/z |
|---|---|---|
| 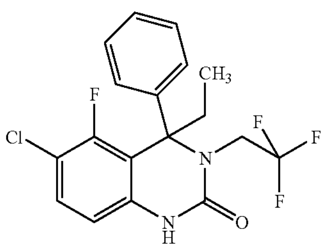 | 6-CHLORO-5-FLUORO-4-ETHYL-4-PHENYL-3-(2,2,2-TRIFLUOROETHYL)-3,4-DIHYDROQUINAZOLIN-2(1H)-ONE | 387.1 |
| 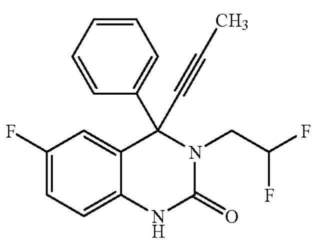 | 6-FLUORO-4-(1-PROPYNYL)-4-PHENYL-3-(2,2-DIFLUOROETHYL)-3,4-DIHYDROQUINAZOLIN-2(1H)-ONE | 345.1 |
| 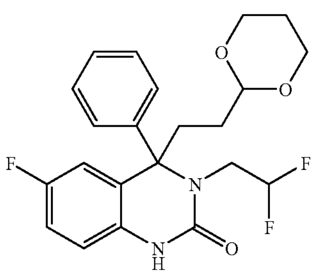 | 3-(2,2-difluoroethyl)-4-[2-(1,3-dioxan-2-yl)ethyl]-6-fluoro-4-phenyl-3,4-dihydroquinazolin-2(1H)-one | 421.3 |
| 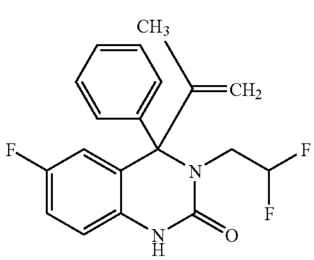 | 6-FLUORO-4-(2-PROPENYL)-4-PHENYL-3-(2,2-DIFLUOROETHYL)-3,4-DIHYDROQUINAZOLIN-2(1H)-ONE | 347.1 |
| 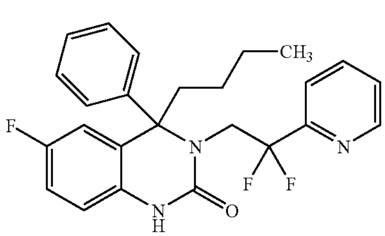 | 6-FLUORO-4-BUTYL-4-PHENYL-3-(2,2-DIFLUOROETHYL)-3,4-DIHYDROQUINAZOLIN-2(1H)-ONE | 440.2 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH$^+$) m/z |
|---|---|---|
| 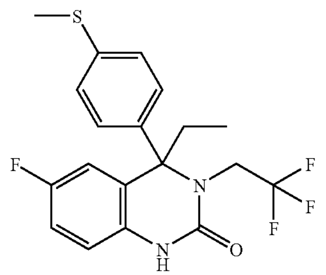 | 6-FLUORO-4-ETHYL-4-(4-THIOMETHYLPHENYL)-3-(2,2,2-TRIFLUOROETHYL)-3,4-DIHYDROQUINAZOLIN-2(1H)-ONE | 399.1 |
| 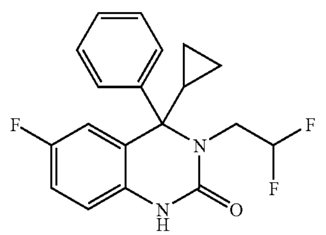 | 6-FLUORO-4-CYCLOPROPYL-4-PHENYL-3-(2,2-DIFLUOROETHYL)-3,4-DIHYDROQUINAZOLIN-2(1H)-ONE | 347.1 |
| 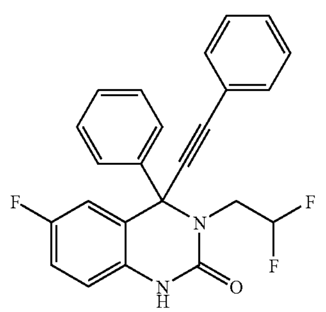 | 3-(2,2-difluoroethyl)-6-fluoro-4-phenyl-4-(phenylethynyl)-3,4-dihydroquinazolin-2(1H)-one | 407.1 |
| 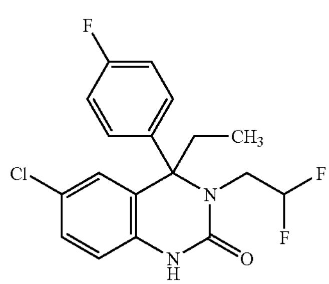 | 6-CHLORO-4-ETHYL-4-(4-FLUOROPHENYL)-3-(2,2-DIFLUOROETHYL)-3,4-DIHYDROQUINAZOLIN-2(1H)-ONE | 369.1 |
| 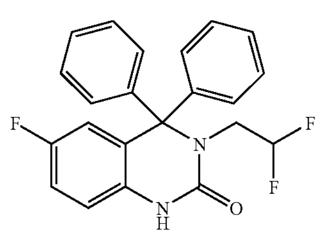 | 6-FLUORO-4,4-DIPHENYL-3-(2,2-DIFLUOROETHYL)-3,4-DIHYDROQUINAZOLIN-2(1H)-ONE | 383.3 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH$^+$) m/z |
|---|---|---|
| 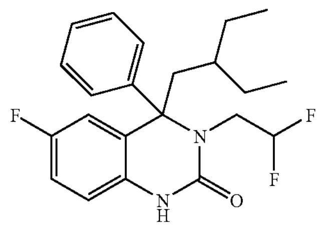 | 3-(2,2-difluoroethyl)-4-(2-ethylbutyl)-6-fluoro-4-phenyl-3,4-dihydroquinazolin-2(1H)-one | 391.2 |
| 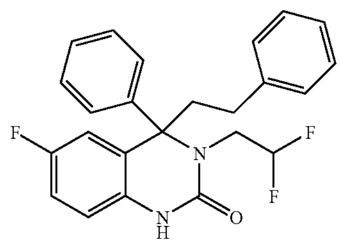 | 3-(2,2-difluoroethyl)-6-fluoro-4-phenyl-4-(2-phenylethyl)-3,4-dihydroquinazolin-2(1H)-one | 411.2 |
| 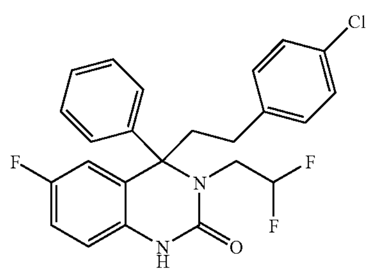 | 3-(2,2-difluoroethyl)-6-fluoro-4-phenyl-4-(2-(4-chlorophenyl)ethyl)-3,4-dihydroquinazolin-2(1H)-one | 445.1 |
| 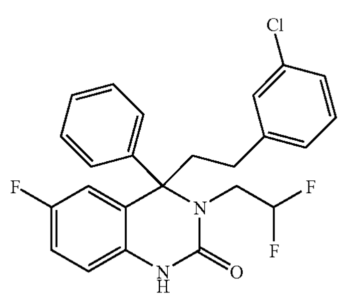 | 3-(2,2-difluoroethyl)-6-fluoro-4-phenyl-4-(2-(3-chlorophenyl)ethyl)-3,4-dihydroquinazolin-2(1H)-one | 445.1 |
| 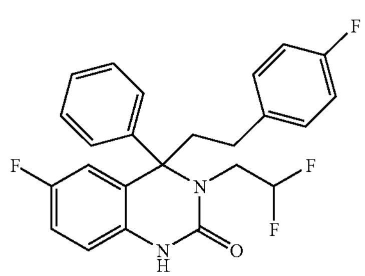 | 3-(2,2-difluoroethyl)-6-fluoro-4-phenyl-4-(2-(4-fluorophenyl)ethyl)-3,4-dihydroquinazolin-2(1H)-one | 429.2 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH+) m/z |
|---|---|---|
| 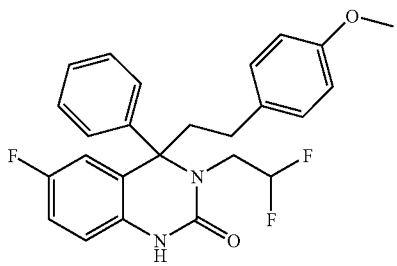 | 3-(2,2-difluoroethyl)-6-fluoro-4-phenyl-4-(2-(4-methoxyphenyl)ethyl)-3,4-dihydroquinazolin-2(1H)-one | 441.2 |
| 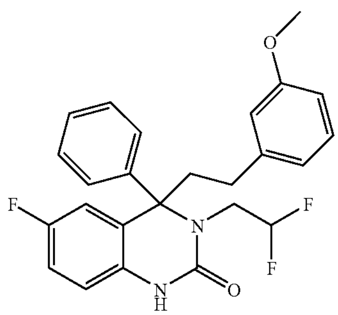 | 3-(2,2-difluoroethyl)-6-fluoro-4-phenyl-4-(2-(3-methoxyphenyl)ethyl)-3,4-dihydroquinazolin-2(1H)-one | 441.2 |
| 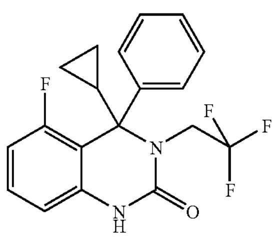 | 5-FLUORO-4-CYCLOPROPYL-4-PHENYL-3-(2,2,2-TRIFLUOROETHYL)-3,4-DIHYDROQUINAZOLIN-2(1H)-ONE | 365.1 |
| 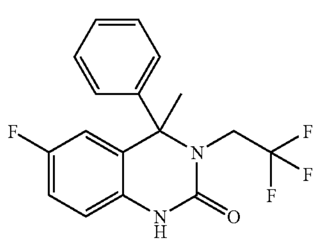 | 6-FLUORO-4-METHYL-4-PHENYL-3-(2,2,2-TRIFLUOROETHYL)-3,4-DIHYDROQUINAZOLIN-2(1H)-ONE | 339.1 |
| 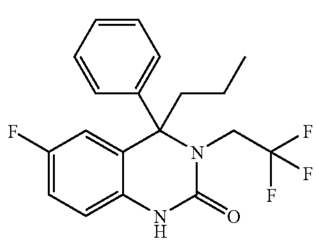 | 6-FLUORO-4-PROPYL-4-PHENYL-3-(2,2,2-TRIFLUOROETHYL)-3,4-DIHYDROQUINAZOLIN-2(1H)-ONE | 367.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH$^+$) m/z |
|---|---|---|
| 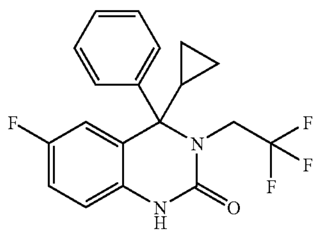 | 6-FLUORO-4-CYCLOPROPYL-4-PHENYL-3-(2,2,2-TRIFLUOROETHYL)-3,4-DIHYDROQUINAZOLIN-2(1H)-ONE | 365.1 |
| 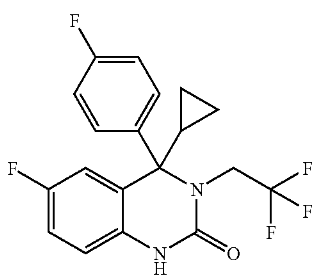 | 6-FLUORO-4-CYCLOPROPYL-4-(4-FLUOROPHENYL)-3-(2,2,2-TRIFLUOROETHYL)-3,4-DIHYDROQUINAZOLIN-2(1H)-ONE | 383.1 |
| 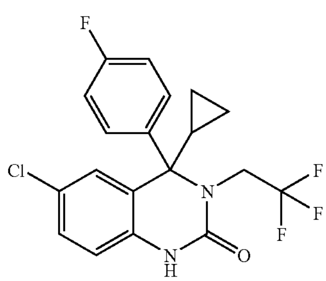 | 6-CHLORO-4-CYCLOPROPYL-4-(4-FLUOROPHENYL)-3-(2,2,2-TRIFLUOROETHYL)-3,4-DIHYDROQUINAZOLIN-2(1H)-ONE | 399.1 |
| 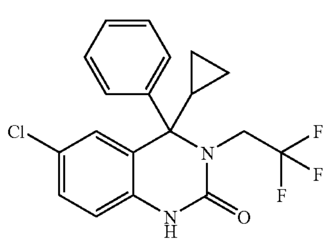 | 6-CHLORO-4-CYCLOPROPYL-4-PHENYL-3-(2,2,2-TRIFLUOROETHYL)-3,4-DIHYDROQUINAZOLIN-2(1H)-ONE | 381.1 |
| 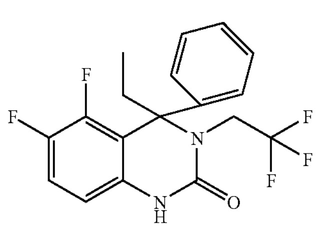 | 5,6-DIFLUORO-4-ETHYL-4-PHENYL-3-(2,2,2-TRIFLUOROETHYL)-3,4-DIHYDROQUINAZOLIN-2(1H)-ONE | 371.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH+) m/z |
|---|---|---|
| 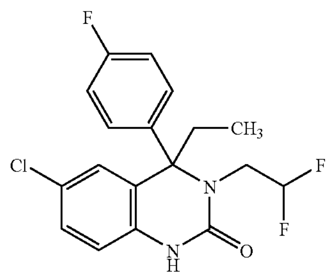 | 6-CHLORO-4-ETHYL-4-(4-FLUOROPHENYL)-3-(2,2-DIFLUOROETHYL)-3,4-DIHYDROQUINAZOLIN-2(1H)-ONE | 369.1 |
| 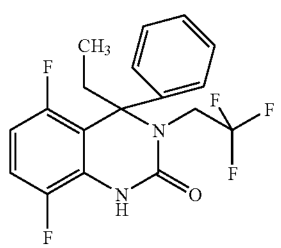 | 5,8-DIFLUORO-4-ETHYL-4-PHENYL-3-(2,2,2-TRIFLUOROETHYL)-3,4-DIHYDROQUINAZOLIN-2(1H)-ONE | 371.1 |
| 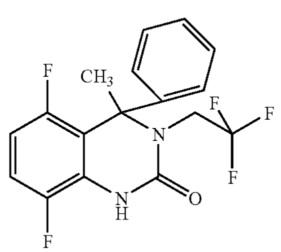 | 5,8-DIFLUORO-4-METHYL-4-PHENYL-3-(2,2,2-TRIFLUOROETHYL)-3,4-DIHYDROQUINAZOLIN-2(1H)-ONE | 357.1 |
| 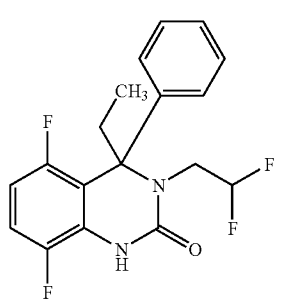 | 5,8-DIFLUORO-4-ETHYL-4-PHENYL-3-(2,2-DIFLUOROETHYL)-3,4-DIHYDROQUINAZOLIN-2(1H)-ONE | 353.1 |
| 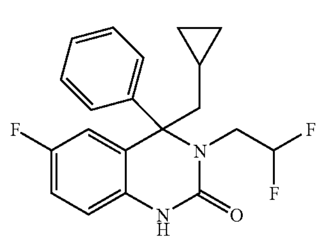 | 6-FLUORO-4-CYCLOPROPYLMETHYL-4-PHENYL-3-(2,2,2-TRIFLUOROETHYL)-3,4-DIHYDROQUINAZOLIN-2(1H)-ONE | 361.2 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH+) m/z |
|---|---|---|
| 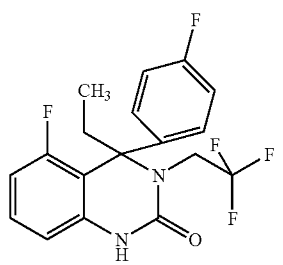 | 5-FLUORO-4-ETHYL-4-PHENYL-3-(2,2,2-TRIFLUOROETHYL)-3,4-DIHYDROQUINAZOLIN-2(1H)-ONE | 371.1 |
| 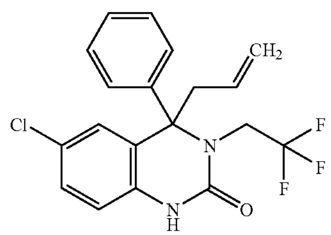 | 6-CHLORO-4-(3-PROPENYL)-4-PHENYL-3-(2,2,2-TRIFLUOROETHYL)-3,4-DIHYDROQUINAZOLIN-2(1H)-ONE | 381.1 |
| 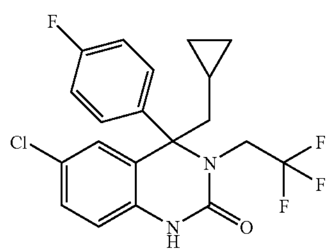 | 6-CHLORO-4-CYCLOPROPYLMETHYL-4-(4-FLUOROPHENYL)-3-(2,2,2-TRIFLUOROETHYL)-3,4-DIHYDROQUINAZOLIN-2(1H)-ONE | 413.1 |
| 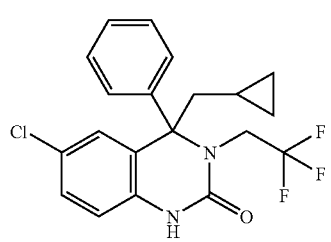 | 6-CHLORO-4-CYCLOPROPYLMETHYL-4-PHENYL-3-(2,2,2-TRIFLUOROETHYL)-3,4-DIHYDROQUINAZOLIN-2(1H)-ONE | 395.1 |
| 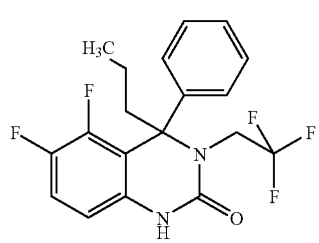 | 5,6-DIFLUORO-4-PROPYL-4-PHENYL-3-(2,2,2-TRIFLUOROETHYL)-3,4-DIHYDROQUINAZOLIN-2(1H)-ONE | 385.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH$^+$) m/z |
|---|---|---|
| 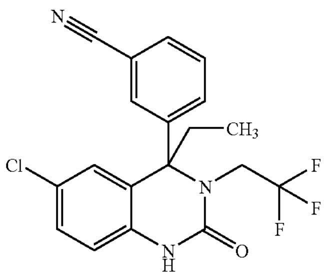 | 6-CHLORO-4-ETHYL-4-(3-CYANOPHENYL)-3-(2,2,2-TRIFLUOROETHYL)-3,4-DIHYDROQUINAZOLIN-2(1H)-ONE | 394.1 |
| 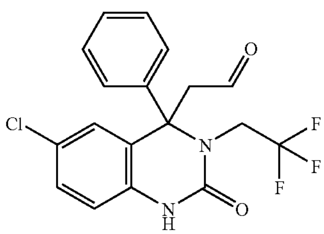 | 6-CHLORO-4-(3-FORMYLMETHYL)-4-PHENYL-3-(2,2,2-TRIFLUOROETHYL)-3,4-DIHYDROQUINAZOLIN-2(1H)-ONE | 383.1 |
| 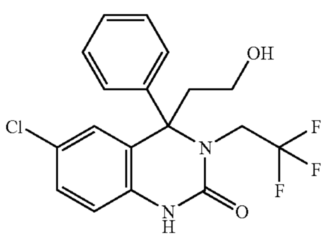 | 6-CHLORO-4-(3-HYDROXYETHYL)-4-PHENYL-3-(2,2,2-TRIFLUOROETHYL)-3,4-DIHYDROQUINAZOLIN-2(1H)-ONE | 385.1 |
| 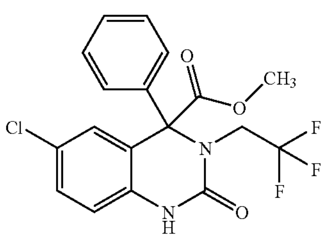 | 6-CHLORO-4-(METHOXYCARBONYL)-4-PHENYL-3-(2,2,2-TRIFLUOROETHYL)-3,4-DIHYDROQUINAZOLIN-2(1H)-ONE | 399.1 |
| 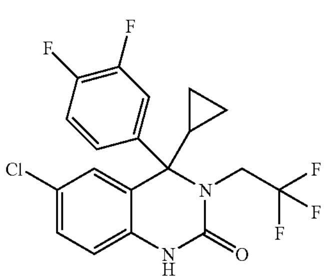 | 6-CHLORO-4-CYCLOPROPYL-4-(3,4-DIFLUOROPHENYL)-3-(2,2,2-TRIFLUOROETHYL)-3,4-DIHYDROQUINAZOLIN-2(1H)-ONE | 417 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH+) m/z |
|---|---|---|
| 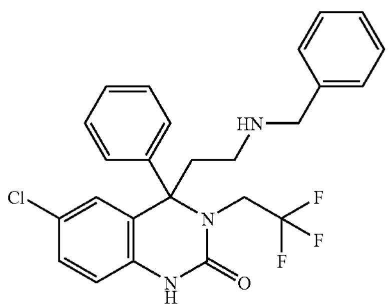 | 4-[2-(benzylamino)ethyl]-6-chloro-4-phenyl-3-(2,2,2-trifluoroethyl)-3,4-dihydroquinazolin-2(1H)-one | 474.1 |
| 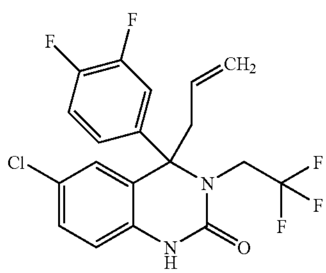 | 6-CHLORO-4-(3-PROPENYL)-4-(3,4-DIFLUOROPHENYL)-3-(2,2,2-TRIFLUOROETHYL)-3,4-DIHYDROQUINAZOLIN-2(1H)-ONE | 417 |
| 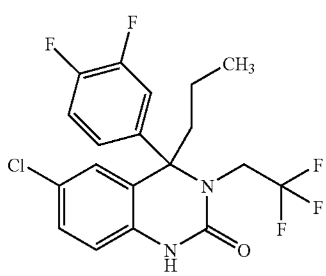 | 6-CHLORO-4-PROPYL-4-(3,4-DIFLUOROPHENYL)-3-(2,2,2-TRIFLUOROETHYL)-3,4-DIHYDROQUINAZOLIN-2(1H)-ONE | 419 |
| 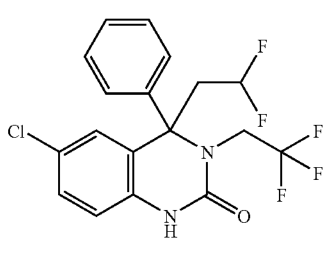 | 6-CHLORO-4-(2,2-DIFLUOROETHYL)-4-PHENYL-3-(2,2,2-TRIFLUOROETHYL)-3,4-DIHYDROQUINAZOLIN-2(1H)-ONE | 405 |
| 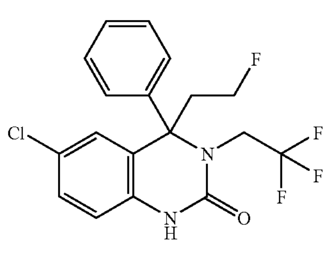 | 6-CHLORO-4-(2-FLUOROETHYL)-4-PHENYL-3-(2,2,2-TRIFLUOROETHYL)-3,4-DIHYDROQUINAZOLIN-2(1H)-ONE | 387 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH$^+$) m/z |
|---|---|---|
| 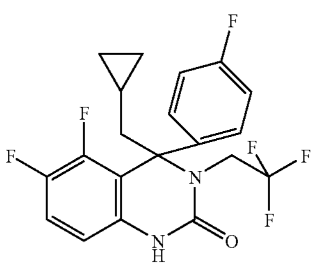 | 5,6-DIFLUORO-4-CYCLOPROPYLMETHYL-4-(4-FLUOROPHENYL)-3-(2,2,2-TRIFLUOROETHYL)-3,4-DIHYDROQUINAZOLIN-2(1H)-ONE | 415 |
| 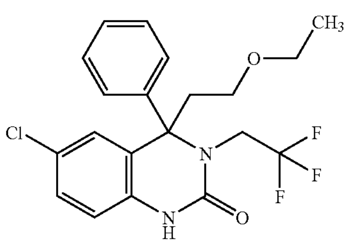 | 6-CHLORO-4-(2-ETHOXYETHYL)-4-PHENYL-3-(2,2,2-TRIFLUOROETHYL)-3,4-DIHYDROQUINAZOLIN-2(1H)-ONE | 413.1 |
| 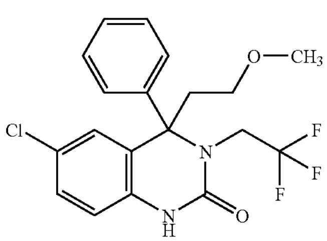 | 6-CHLORO-4-(2-METHOXYETHYL)-4-PHENYL-3-(2,2,2-TRIFLUOROETHYL)-3,4-DIHYDROQUINAZOLIN-2(1H)-ONE | 399.1 |
| 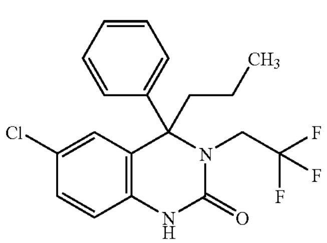 | 6-CHLORO-4-PROPYL-4-PHENYL-3-(2,2,2-TRIFLUOROETHYL)-3,4-DIHYDROQUINAZOLIN-2(1H)-ONE | 383.1 |
| 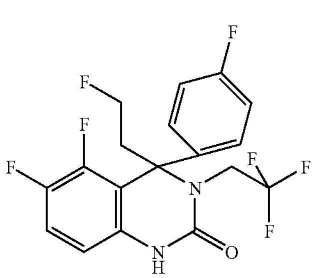 | 5,6-DIFLUORO-4-(2-FLUOROETHYL)-4-(4-FLUOROPHENYL)-3-(2,2,2-TRIFLUOROETHYL)-3,4-DIHYDROQUINAZOLIN-2(1H)-ONE | 407.0 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH$^+$) m/z |
|---|---|---|
| 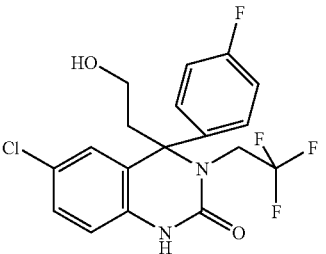 | 6-CHLORO-4-(2HYDROXYETHYL)-4-(4-FLUOROPHENYL)-3-(2,2,2-TRIFLUOROETHYL)-3,4-DIHYDROQUINAZOLIN-2(1H)-ONE | 403 |
| 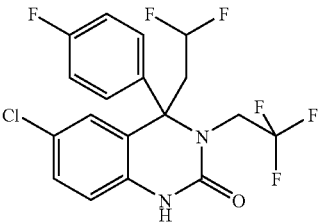 | 6-CHLORO-4-(2,2-DIFLUOROETHYL)-4-(4-FLUOROPHENYL)-3-(2,2,2-TRIFLUOROETHYL)-3,4-DIHYDROQUINAZOLIN-2(1H)-ONE | 423.0 |
| 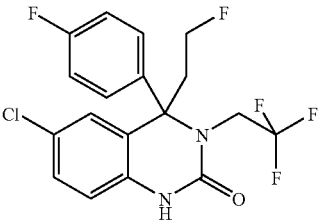 | 6-CHLORO-4-(2-FLUOROETHYL)-4-(4-FLUOROPHENYL)-3-(2,2,2-TRIFLUOROETHYL)-3,4-DIHYDROQUINAZOLIN-2(1H)-ONE | 405 |
| 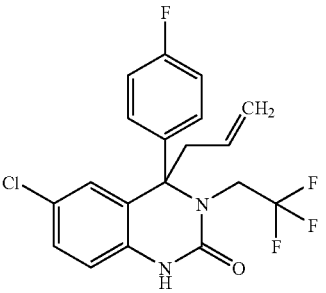 | 6-CHLORO-4-(3-PROPENYL)-4-(4-FLUOROPHENYL)-3-(2,2,2-TRIFLUOROETHYL)-3,4-DIHYDROQUINAZOLIN-2(1H)-ONE | 399 |

EXAMPLE 22

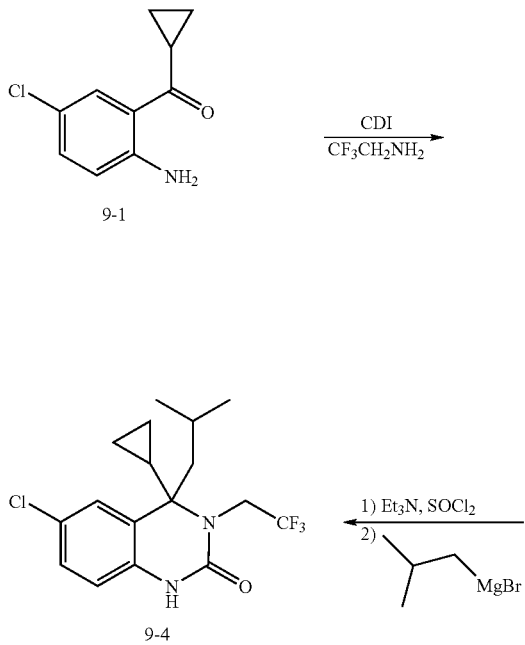

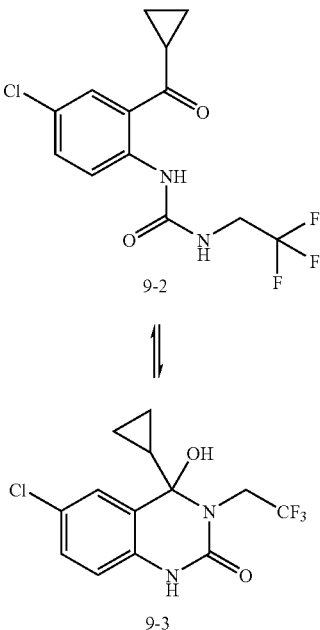

N-[4-chloro-2-(cyclopropylcarbonyl)phenyl]-N'-(2,2,2-trifluoroethyl)urea (9-2)

To a solution of 0.51 g (2.6 mmol) (2-amino-5-chlorophenyl)(cyclopropyl)-methanone (4-1, Tetrahedron Lett 1994, 35, 6811) in 5 mL 1,2-dichloroethane was added 0.5 g (3.1 mmol) carbonyldiimidazole and the reaction mixture heated to 60 degrees for 18 hours. Upon cooling to room temperature, 0.31 mL (3.9 mmol) 2,2,2-trifluoroethylamine was added and the reaction mixture heated to 60 degrees another 18 hours. Upon cooling the mixture was diluted with 100 mL CH2Cl2, washed with 100 mL each of 10% KHSO$_4$, water and brine then dried over MgSO$_4$ and concentrated to give N-[4-chloro-2-(cyclopropyl-carbonyl)-phenyl]-N'-(2,2,2-trifluoroethyl)urea. 1H NMR (CDCl$_3$, 400 MHz) 11.06 (s, 1H); 8.49 (d, J=8.97 Hz, 1H); 8.03 (d, J=2.39 Hz, 1H); 7.47 (dd, J=2.56 and 9.15 Hz, 1H); 5.00 (t, J=6.08 Hz, 1H); 3.93 (dq, J=6.59 and 8.97 Hz, 2H); 2.64 (tt, J=4.58 and 7.88 Hz, 1H); 1.26 (m, 2H); 1.39 (m, 2H). Electrospray mass spectrum M+H=321.0.

6-chloro-4-cyclopropyl-4-hydroxy-3-(2,2,2-trifluoroethyl)-3,4-dihydroquinazolin-2 (1H 9-3)

To a 0° C. solution of 0.33 g (1 mmol) N-[4-chloro-2-(cyclopropylcarbonyl)-phenyl]-N'-(2,2,2-trifluoroethyl)urea was added 0.091 g (2.2 mmol, 60% dispersion in mineral oil) sodium hydride and the reaction mixture was allowed to warm to room temperature and stir 16 hours. The reaction was quenched with 100 mL saturated aqueous NH$_4$Cl solution and extracted with 200 mL EtOAc. The extract was washed with 100 mL brine, dried over MgSO$_4$, filtered, and concentrated. Purification by automated flash chromatography (40 g silica gel cartridge, 10-50% EtOAc/hexanes over 15 min) afforded 223 mg starting ketone and 83 mg of 6-chloro-4-cyclopropyl-4-hydroxy-3-(2,2,2-trifluoroethyl)-3,4-dihydroquinazolin-2(1H)-one. 1H NMR (CDCl$_3$, 400 MHz) 7.74 (s, 1H); 7.41 (d, J=2.19 Hz, 1H); 7.27 (dd, obscured by CHCl$_3$, 1H); 6.74 (d, J=8.42 Hz, 1H); 4.6 (m, 1H); 4.15 (m, 1H); 1.20 (m, 1H); 0.86 (m, 1H); 0.64 (m, 1H); 0.44 (m, 2H). Electrospray mass spectrum M+H=321.0

6-chloro-4-cyclopropyl-4-isobutyl-3-(2,2,2-trifluoroethyl)-3,4-dihydroquinazolin-2(1H)-one (9-4)

To a 0° C. solution of 0.08 g (0.25 mmol) 6-chloro-4-cyclopropyl-4-hydroxy-3-(2,2,2-trifluoroethyl)-3,4-dihydroquinazolin-2(1H)-one in 3 mL toluene was added 0.17 mL (1.25 mmol) Et3N and 0.018 mL (0.25 mmol) SOCl$_2$. After 20 min at 0° C. 1 mL (1 mmol, 1M solution in ether) isobutyl magnesium bromide was added and the reaction mixture was stirred 30 minutes before an additional 0.5 mL (0.5 mmol) isobutyl magnesium bromide was added and the reaction mixture was allowed to warm to room temperature. The reaction mixture was quenched with 75 mL saturated aqueous NH$_4$Cl solution and extracted with 100 mL EtOAc. The extract was washed with 75 mL brine, dried over MgSO4, filtered, and concentrated. Purification by flash chromatography (1×10 cm silica gel, linear gradient 10-35% EtOAc/hexanes) followed by preparative HPLC (YMC C18 PRO20×150 mm, linear gradient 5-95% CH3CN/H2O 0.05% added TFA, over 30 min) to afford afforded 6-chloro-4-cyclopropyl-4-isobutyl-3-(2,2,2-trifluoroethyl)-3,4-dihydroquinazolin-2 (1H)-one. 1H NMR (CDCl$_3$, 400 MHz) 8.17 (s, 1H); 7.43 (d, J=2.20 Hz, 1H); 7.15 (dd, J=2.38 and 8.61 Hz, 1H); 6.62 (d, J=8.42 Hz, 1H); 4.50 (dq, J=15.4 and 8.61 Hz, 1H); 3.96 (dq, J=15.4 and 8.60 Hz, 1H); 1.56 (m, 1H); 1.41 (dd, J=14.8 and 5.31 Hz, 1H); 1.23 (dd, J=14.8 and 5.68 Hz, 1H); 0.88 (m, 1H); 0.80 (d, J=6.59 Hz, 3H); 0.78 (m, 1H); 0.69 (m, 2H); 0.55 (d, J=6.59 Hz, 3H). High resolution mass spec (FT/ICR): calc M$^+$H=361.1289, found 361.1283.

TABLE 2

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | NAME | parent ion (MH$^+$) m/z |
|---|---|---|
| 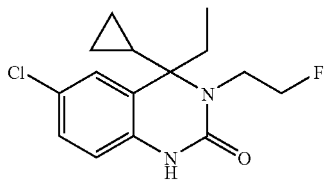 | 6-CHLORO-4-CYCLOPROPYL-4-ETHYL-3-(2-FLUOROETHYL)-3,4-DIHYDROQUINAZOLIN-2(1H)-ONE | 297.1 |
| 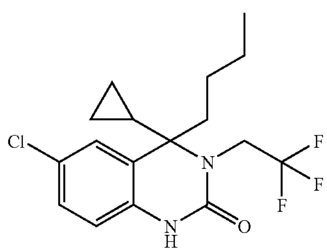 | 4-BUTYL-6-CHLORO-4-CYCLOPROPYL-3-(2,2,2-TRIFLUOROETHYL)-3,4-DIHYDROQUINAZOLIN-2(1H)-ONE | 361.1 |
| 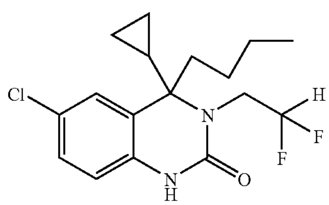 | 4-butyl-6-chloro-4-cyclopropyl-3-(2,2-difluoroethyl)-3,4-dihydroquinazolin-2(1H)-one | 343.1 |
| 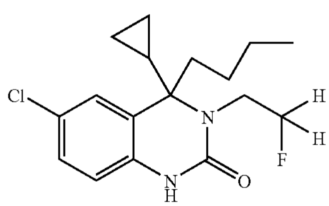 | 4-butyl-6-chloro-4-cyclopropyl-3-(2-fluoroethyl)-3,4-dihydroquinazolin-2(1H)-one | 325.1 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound which is selected from the group consisting of:
   4-(2,2-Difluoroethyl)-5,6-difluoro-4-(4-fluorophenyl)-3-(2,2,2-trifluoroethyl)-3,4-dihydroquinazolin-2(1H)-one;
   6-Chloro-4-ethyl-4-(4-fluorophenyl)-3-(2,2,2-trifluoroethyl)-3,4-dihydroquinazolin-2(1H)-one;
   6-Chloro-4-(4-fluorophenyl)-4-propyl-3-(2,2,2-trifluoroethyl)-3,4-dihydroquinazolin-2(1H)-one; and
   6-Chloro-4-cyclopropyl-4-(4-cyanophenyl)-3-(2,2,2-trifluoroethyl)-3,4-dihydroquinazolin-2(1H)-one;
   or a pharmaceutically acceptable salt thereof.

2. The compound of claim 1 which is 4-(2,2-Difluoroethyl)-5,6-difluoro-4-(4-fluorophenyl)-3-(2,2,2-trifluoroethyl)-3,4-dihydroquinazolin-2(1H)-one, or a pharmaceutically acceptable salt thereof.

3. The compound of claim 1 which is 6-Chloro-4-ethyl-4-(4-fluorophenyl)-3-(2,2,2-trifluoroethyl)-3,4-dihydroquinazolin-2(1H)-one, or a pharmaceutically acceptable salt thereof.

4. The compound of claim 1 which is 6-Chloro-4-(4-fluoro-phenyl)-4-propyl-3-(2,2,2-trifluoroethyl)-3,4-dihydroquinazolin-2(1H)-one, or a pharmaceutically acceptable salt thereof.

5. A compound which is 6-Chloro-4-cyclopropyl-4-(4-cyanophenyl)-3-(2,2,2-trifluoroethyl)-3,4-dihydroquinazolin-2(1H)-one, or a pharmaceutically acceptable salt thereof.

6. A compound which is 6-Chloro-4-cyclopropyl-4-(4-cyanophenyl)-3-(2,2,2-trifluoroethyl)-3,4-dihydroquinazolin-2(1H)-one.

7. A pharmaceutical composition which comprises a pharmaceutically acceptable carrier and the compound of claim 1, or a pharmaceutically acceptable salt thereof.

8. A pharmaceutical composition which comprises a pharmaceutically acceptable carrier and the compound of claim 2, or a pharmaceutically acceptable salt thereof.

9. A pharmaceutical composition which comprises a pharmaceutically acceptable carrier and the compound of claim 3, or a pharmaceutically acceptable salt thereof.

10. A pharmaceutical composition which comprises a pharmaceutically acceptable carrier and the compound of claim 4, or a pharmaceutically acceptable salt thereof.

11. A pharmaceutical composition which comprises a pharmaceutically acceptable carrier and the compound of claim 5, or a pharmaceutically acceptable salt thereof.

12. A pharmaceutical composition which comprises a pharmaceutically acceptable carrier and the compound of claim 6.

* * * * *